United States Patent
Hodi et al.

(10) Patent No.: US 10,837,966 B2
(45) Date of Patent: Nov. 17, 2020

(54) ANTI-GALECTIN ANTIBODY BIOMARKERS PREDICTIVE OF ANTI-IMMUNE CHECKPOINT AND ANTI-ANGIOGENESIS RESPONSES

(71) Applicant: Dana-Farber Cancer Institute, Inc., Boston, MA (US)

(72) Inventors: F. Stephen Hodi, Framingham, MA (US); Xinqi Wu, Chestnut Hill, MA (US); Jingjing Li, Lexington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/523,519

(22) PCT Filed: Oct. 30, 2015

(86) PCT No.: PCT/US2015/058276
§ 371 (c)(1),
(2) Date: May 1, 2017

(87) PCT Pub. No.: WO2016/073299
PCT Pub. Date: May 12, 2016

(65) Prior Publication Data
US 2017/0343552 A1 Nov. 30, 2017

Related U.S. Application Data

(60) Provisional application No. 62/074,779, filed on Nov. 4, 2014.

(51) Int. Cl.
| | | |
|---|---|---|
| G01N 33/573 | (2006.01) | |
| G01N 33/574 | (2006.01) | |
| C07K 16/22 | (2006.01) | |
| C07K 16/28 | (2006.01) | |
| A61P 35/00 | (2006.01) | |
| C07K 16/06 | (2006.01) | |
| C07K 16/30 | (2006.01) | |
| A61K 39/00 | (2006.01) | |

(52) U.S. Cl.
CPC ........ *G01N 33/57488* (2013.01); *A61P 35/00* (2018.01); *C07K 16/06* (2013.01); *C07K 16/22* (2013.01); *C07K 16/2818* (2013.01); *C07K 16/2851* (2013.01); *C07K 16/30* (2013.01); *A61K 2039/507* (2013.01); *C07K 2317/76* (2013.01)

(58) Field of Classification Search
None
See application file for complete search history.

(56) References Cited

U.S. PATENT DOCUMENTS

2009/0311187 A1 12/2009 Berman et al.
2014/0227286 A1 8/2014 Jaffee et al.

FOREIGN PATENT DOCUMENTS

WO WO-2012/131079 A1 10/2012

OTHER PUBLICATIONS

Hodi et al, Cancer Immunoll Res 2:632-642, 2014. (Year: 2014) IDS filed on May 1, 2017.*
Hodi et al (Cancer Immunol Res 2: 632-642, online published Apr. 21, 2014 (Year: 2014).*
Extended European Search Report issued by the European Patent Office in corresponding Application No. EP 15856996.2, dated Mar. 20, 2018.
Song et al., "Galectin-3 in cancer," Clin Chim Acta, 431:185-191 (2014).
Wu et al., "Combined anti-VEGF and anti-CTlA-4 therapy elicits humoral immunity to galectin-1 which is associated with favorable clinical outcomes," Cancer Immunol Res, 5(6):446-454 (2017).
Yuan et al., "Pretreatment serum VEGF is associated with clinical response and overall survival in advanced melanoma patients treated with ipilimumab," Cancer Immunol Res, 2(2):127-132 (2014).
Hodi et al., "Bevacizumab plus ipilimumab in patients with metastatic melanoma," Cancer Immunol Res, 2(7): 632-642 (2014).
International Search Report and Written Opinion for International Application No. PCT/US15/58276 dated Feb. 5, 2016.

* cited by examiner

*Primary Examiner* — Lei Yao
(74) *Attorney, Agent, or Firm* — Foley Hoag LLP

(57) ABSTRACT

The present invention is based on the identification of novel biomarkers predictive of responsiveness to a combination of anti-immune checkpoint and anti-angiogenesis therapies.

17 Claims, 6 Drawing Sheets
Specification includes a Sequence Listing.

SEQUENCE LISTING

```
<160> NUMBER OF SEQ ID NOS: 28

<210> SEQ ID NO 1
<211> LENGTH: 408
<212> TYPE: DNA
<213> ORGANISM: Homo sapiens

<400> SEQUENCE: 1
atggcttgtg gtctggtcgc cagcaacctg aatctcaaac ctggagagtg ccttcgagtg        60
cgaggcgagg tggctcctga cgctaagagc ttcgtgctga acctgggcaa agacagcaac       120
aacctgtgcc tgcacttcaa ccctcgcttc aacgcccacg gcgacgccaa caccatcgtg       180
tgcaacagca aggacggcgg ggcctggggg accgagcagc gggaggctgt ctttcccttc       240
cagcctggaa gtgttgcaga ggtgtgcatc accttcgacc aggccaacct gaccgtcaag       300
```

```
ctgccagatg gatacgaatt caagttcccc aaccgcctca acctggaggc catcaactac    360
atggcagctg acggtgactt caagatcaaa tgtgtggcct ttgactga                 408
```

<210> SEQ ID NO 2
<211> LENGTH: 135
<212> TYPE: PRT
<213> ORGANISM: Homo sapiens

<400> SEQUENCE: 2

```
Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
        130                 135
```

<210> SEQ ID NO 3
<211> LENGTH: 408
<212> TYPE: DNA
<213> ORGANISM: Mus musculus

<400> SEQUENCE: 3

```
atggcctgtg gtctggtcgc cagcaacctg aatctcaaac ctggggaatg tctcaaagtt    60
cggggagagg tggcctcgga cgccaagagc tttgtgctga acctgggaaa agacagcaac   120
aacctgtgcc tacacttcaa tcctcgcttc aatgcccatg gagacgccaa caccattgtg   180
tgtaacacca aggaagatgg gacctgggga accgaacacg gggaacctgc cttccccttc   240
cagcccggga gcatcacaga ggtgtgcatc acctttgacc aggctgacct gaccatcaag   300
ctgccagacg gacatgaatt caagttcccc aaccgcctca acatggaggc catcaactac   360
atggcggcgg atggagactt caagattaag tgcgtggcct ttgagtga                408
```

<210> SEQ ID NO 4
<211> LENGTH: 135
<212> TYPE: PRT
<213> ORGANISM: Mus musculus

<400> SEQUENCE: 4

```
Met Ala Cys Gly Leu Val Ala Ser Asn Leu Asn Leu Lys Pro Gly Glu
1               5                   10                  15

Cys Leu Lys Val Arg Gly Glu Val Ala Ser Asp Ala Lys Ser Phe Val
            20                  25                  30

Leu Asn Leu Gly Lys Asp Ser Asn Asn Leu Cys Leu His Phe Asn Pro
        35                  40                  45
```

```
Arg Phe Asn Ala His Gly Asp Ala Asn Thr Ile Val Cys Asn Thr Lys
         50                  55                  60
Glu Asp Gly Thr Trp Gly Thr Glu His Arg Glu Pro Ala Phe Pro Phe
 65                  70                  75                  80
Gln Pro Gly Ser Ile Thr Glu Val Cys Ile Thr Phe Asp Gln Ala Asp
                 85                  90                  95
Leu Thr Ile Lys Leu Pro Asp Gly His Glu Phe Lys Phe Pro Asn Arg
            100                 105                 110
Leu Asn Met Glu Ala Ile Asn Tyr Met Ala Ala Asp Gly Asp Phe Lys
        115                 120                 125
Ile Lys Cys Val Ala Phe Glu
        130             135
```

<210> SEQ ID NO 5
<211> LENGTH: 753
<212> TYPE: DNA
<213> ORGANISM: Homo sapiens

<400> SEQUENCE: 5

```
atggcagaca atttttcgct ccatgatgcg ttatctgggt ctggaaaccc aaaccctcaa      60
ggatggcctg gcgcatgggg gaaccagcct gctggggcag ggggctaccc aggggcttcc     120
tatcctgggg cctaccccgg gcaggcaccc caggggcttt atcctggaca ggcacctcca     180
ggcgcctacc ctggagcacc tggagcttat cccggagcac tgcacctgg agtctaccca      240
gggccaccca gcggccctgg ggcctaccca tcttctggac agccaagtgc accggagcc      300
taccctgcca ctggccccta tggcgcccct gctgggccac tgattgtgcc ttataacctg     360
cctttgcctg ggggagtggt gcctcgcatg ctgataacaa ttctgggcac ggtgaagccc     420
aatgcaaaca gaattgcttt agatttccaa agagggaatg atgttgcctt ccactttaac     480
ccacgcttca atgagaacaa caggagagtc attgtttgca atacaaagct ggataataac     540
tggggaaggg aagaaagaca gtcggttttc ccatttgaaa gtgggaaacc attcaaaata     600
caagtactgg ttgaacctga ccacttcaag gttgcagtga tgatgctca cttgttgcag      660
tacaatcatc gggttaaaaa actcaatgaa atcagcaaac tgggaatttc tggtgacata     720
gacctcacca gtgcttcata taccatgata taa                                  753
```

<210> SEQ ID NO 6
<211> LENGTH: 250
<212> TYPE: PRT
<213> ORGANISM: Homo sapiens

<400> SEQUENCE: 6

```
Met Ala Asp Asn Phe Ser Leu His Asp Ala Leu Ser Gly Ser Gly Asn
  1               5                  10                  15
Pro Asn Pro Gln Gly Trp Pro Gly Ala Trp Gly Asn Gln Pro Ala Gly
             20                  25                  30
Ala Gly Gly Tyr Pro Gly Ala Ser Tyr Pro Gly Ala Tyr Pro Gly Gln
         35                  40                  45
Ala Pro Pro Gly Ala Tyr Pro Gly Gln Ala Pro Pro Gly Ala Tyr Pro
 50                  55                  60
Gly Ala Pro Gly Ala Tyr Pro Gly Ala Pro Ala Pro Gly Val Tyr Pro
 65                  70                  75                  80
Gly Pro Pro Ser Gly Pro Gly Ala Tyr Pro Ser Ser Gly Gln Pro Ser
                 85                  90                  95
Ala Thr Gly Ala Tyr Pro Ala Thr Gly Pro Tyr Gly Ala Pro Ala Gly
```

```
            100                 105                 110
Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
            180                 185                 190

Glu Ser Gly Lys Pro Phe Lys Ile Gln Val Leu Val Glu Pro Asp His
        195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

Asp Leu Thr Ser Ala Ser Tyr Thr Met Ile
                245                 250

<210> SEQ ID NO 7
<211> LENGTH: 603
<212> TYPE: DNA
<213> ORGANISM: Homo sapiens

<400> SEQUENCE: 7
atggcagaca attttcgct ccatgatgcg ttatctgggt ctggaaaccc aaaccctcaa      60
ggatggcctg gcgcatgggg gaaccagcct gctggggcag ggggctaccc aggggcttcc    120
tatcctgggg cctaccccgg gcaggcaccc ccaggggctt atcctggaca ggcacctcca    180
ggcgcctacc ctggagcacc tggagcttat cccggagcac ctgcacctgg agtctaccca    240
gggccaccca gcggccctgg ggcctaccca tcttctggac agccaagtgc caccggagcc    300
taccctgcca ctggccccta tggcgcccct gctgggccac tgattgtgcc ttataacctg    360
cctttgcctg ggggagtggt gcctcgcatg ctgataacaa ttctgggcac ggtgaagccc    420
aatgcaaaca gaattgcttt agatttccaa agagggaatg atgttgcctt ccactttaac    480
ccacgcttca atgagaacaa caggagagtc attgtttgca cttacatgtg taaaggtttc    540
atgttcactg tgagtgaaaa ttttttacatt catcaatatc cctcttgtaa gtcatctact    600
taa                                                                   603

<210> SEQ ID NO 8
<211> LENGTH: 200
<212> TYPE: PRT
<213> ORGANISM: Homo sapiens

<400> SEQUENCE: 8

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr Pro
    50                  55                  60
```

Gly Ala Pro Gly Ala Tyr Pro Gly Ala Pro Pro Gly Val Tyr Pro
 65                  70                  75                  80

Gly Pro Pro Ser Gly Pro Gly Ala Tyr Pro Ser Ser Gly Gln Pro Ser
                 85                  90                  95

Ala Thr Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Thr Tyr Met
                165                 170                 175

Cys Lys Gly Phe Met Phe Thr Val Ser Glu Asn Phe Tyr Ile His Gln
            180                 185                 190

Tyr Pro Ser Cys Lys Ser Ser Thr
        195                 200

<210> SEQ ID NO 9
<211> LENGTH: 795
<212> TYPE: DNA
<213> ORGANISM: Mus musculus

<400> SEQUENCE: 9
atggcagaca gcttttcgct taacgatgcc ttagctggct ctggaaaccc aaaccctcaa       60
ggatatccgg gtgcatgggg gaaccagcct ggggcagggg gctacccagg ggctgcttat      120
cctggggcct acccaggaca agctcctcca ggggcctacc caggacaggc tcctccaggg      180
gcctacccag acaggctcc tcctagtgcc taccccggcc caactgcccc tggagcttat       240
cctggcccaa ctgcccctgg agcttatcct ggctcaactg ccctggagc cttcccaggg       300 caacctgggg cacctggggc ctaccccagt gctcctggag gctatcctgc tgctggccct      360
tatggtgtcc ccgctggacc actgacggtg ccctatgacc tgcccttgcc tggaggagtc      420
atgccccgca tgctgatcac aatcatgggc acagtgaaac ccaacgcaaa caggattgtt      480
ctagatttca ggagagggaa tgatgttgcc ttccactttg accccgcttc aatgagaac       540 aacaggagag tcattgtgtg taacacgaag caggacaata ctggggaaa ggaagaaaga       600 cagtcagcct tccctttga gagtggcaaa ccattcaaaa tacaagtcct ggttgaagct       660
gaccacttca aggttgcggt caacgatgct cacctactgc agtacaacca tcggatgaag      720
aacctccggg aaatcagcca actggggatc agtggtgaca taaccctcac cagcgctaac      780
cacgccatga tctaa                                                      795

<210> SEQ ID NO 10
<211> LENGTH: 264
<212> TYPE: PRT
<213> ORGANISM: Mus musculus

<400> SEQUENCE: 10

Met Ala Asp Ser Phe Ser Leu Asn Asp Ala Leu Ala Gly Ser Gly Asn
1               5                   10                  15

Pro Asn Pro Gln Gly Tyr Pro Gly Ala Trp Gly Asn Gln Pro Gly Ala
            20                  25                  30

Gly Gly Tyr Pro Gly Ala Ala Tyr Pro Gly Ala Tyr Pro Gly Gln Ala
        35                  40                  45

Pro Pro Gly Ala Tyr Pro Gly Gln Ala Pro Pro Gly Ala Tyr Pro Gly
        50                  55                  60

Gln Ala Pro Pro Ser Ala Tyr Pro Gly Pro Thr Ala Pro Gly Ala Tyr
65                  70                  75                  80

Pro Gly Pro Thr Ala Pro Gly Ala Tyr Pro Gly Ser Thr Ala Pro Gly
                85                  90                  95

Ala Phe Pro Gly Gln Pro Gly Ala Pro Gly Ala Tyr Pro Ser Ala Pro
                100                 105                 110

Gly Gly Tyr Pro Ala Ala Gly Pro Tyr Gly Val Pro Ala Gly Pro Leu
            115                 120                 125

Thr Val Pro Tyr Asp Leu Pro Leu Pro Gly Gly Val Met Pro Arg Met
        130                 135                 140

Leu Ile Thr Ile Met Gly Thr Val Lys Pro Asn Ala Asn Arg Ile Val
145                 150                 155                 160

Leu Asp Phe Arg Arg Gly Asn Asp Val Ala Phe His Phe Asn Pro Arg
                165                 170                 175

Phe Asn Glu Asn Asn Arg Arg Val Ile Val Cys Asn Thr Lys Gln Asp
                180                 185                 190

Asn Asn Trp Gly Lys Glu Glu Arg Gln Ser Ala Phe Pro Phe Glu Ser
                195                 200                 205

Gly Lys Pro Phe Lys Ile Gln Val Leu Val Glu Ala Asp His Phe Lys
            210                 215                 220

Val Ala Val Asn Asp Ala His Leu Leu Gln Tyr Asn His Arg Met Lys
225                 230                 235                 240

Asn Leu Arg Glu Ile Ser Gln Leu Gly Ile Ser Gly Asp Ile Thr Leu
                245                 250                 255

Thr Ser Ala Asn His Ala Met Ile
            260

<210> SEQ ID NO 11
<211> LENGTH: 795
<212> TYPE: DNA
<213> ORGANISM: Mus musculus

<400> SEQUENCE: 11
atggcagaca gcttttcgct taacgatgcc ttagctggct ctggaaaccc aaaccctcaa      60
ggatatccgg gtgcatgggg gaaccagcct ggggcagggg gctacccagg ggctgcttat     120
cctggggcct acccaggaca agctcctcca ggggcctacc caggacaggc tcctccaggg     180
gcctacccag acaggctcc tcctagtgcc taccccggcc caactgcccc tggagcttat      240
cctggcccaa ctgcccctgg agcttatcct ggctcaactg cccctggagc cttcccaggg     300
caacctgggg cacctggggc ctaccccagt gctcctggag gctatcctgc tgctggccct     360
tatggtgtcc ccgctggacc actgacggtg ccctatgacc tgcccttgcc tggaggagtc     420
atgccccgca tgctgatcac aatcatgggc acagtgaaac ccaacgcaaa caggattgtt     480
ctagatttca ggagagggaa tgatgttgcc ttccacttta accccgctt caatgagaac      540 aacaggagag tcattgtgtg taacacgaag caggacaata actggggaaa ggaagaaaga     600
cagtcagcct tccccttga gagtggcaaa ccattcaaaa tacaagtcct ggttgaagct      660
gaccacttca aggttgcggt caacgatgct cacctactgc agtacaacca tcggatgaag     720
aacctccggg aaatcagcca actggggatc agtggtgaca taaccctcac cagcgctaac     780
cacgccatga tctaa                                                     795

<210> SEQ ID NO 12
<211> LENGTH: 264
<212> TYPE: PRT
<213> ORGANISM: Mus musculus

<400> SEQUENCE: 12

Met Ala Asp Ser Phe Ser Leu Asn Asp Ala Leu Ala Gly Ser Gly Asn
1               5                   10                  15

Pro Asn Pro Gln Gly Tyr Pro Gly Ala Trp Gly Asn Gln Pro Gly Ala
            20                  25                  30

Gly Gly Tyr Pro Gly Ala Ala Tyr Pro Gly Ala Tyr Pro Gly Gln Ala
        35                  40                  45

Pro Pro Gly Ala Tyr Pro Gly Gln Ala Pro Pro Gly Ala Tyr Pro Gly
    50                  55                  60

Gln Ala Pro Pro Ser Ala Tyr Pro Gly Pro Thr Ala Pro Gly Ala Tyr
65                  70                  75                  80

Pro Gly Pro Thr Ala Pro Gly Ala Tyr Pro Gly Ser Thr Ala Pro Gly
                85                  90                  95

Ala Phe Pro Gly Gln Pro Gly Ala Pro Gly Ala Tyr Pro Ser Ala Pro
            100                 105                 110

Gly Gly Tyr Pro Ala Ala Gly Pro Tyr Gly Val Pro Ala Gly Pro Leu
        115                 120                 125

Thr Val Pro Tyr Asp Leu Pro Leu Pro Gly Gly Val Met Pro Arg Met
    130                 135                 140

Leu Ile Thr Ile Met Gly Thr Val Lys Pro Asn Ala Asn Arg Ile Val
145                 150                 155                 160

Leu Asp Phe Arg Arg Gly Asn Asp Val Ala Phe His Phe Asn Pro Arg
                165                 170                 175

Phe Asn Glu Asn Asn Arg Arg Val Ile Val Cys Asn Thr Lys Gln Asp
            180                 185                 190

Asn Asn Trp Gly Lys Glu Glu Arg Gln Ser Ala Phe Pro Phe Glu Ser
        195                 200                 205

Gly Lys Pro Phe Lys Ile Gln Val Leu Val Glu Ala Asp His Phe Lys
    210                 215                 220

Val Ala Val Asn Asp Ala His Leu Leu Gln Tyr Asn His Arg Met Lys
225                 230                 235                 240

Asn Leu Arg Glu Ile Ser Gln Leu Gly Ile Ser Gly Asp Ile Thr Leu
                245                 250                 255

Thr Ser Ala Asn His Ala Met Ile
            260

<210> SEQ ID NO 13
<211> LENGTH: 1068
<212> TYPE: DNA
<213> ORGANISM: Homo sapiens

<400> SEQUENCE: 13
atggccttca gcggttccca ggctccctac ctgagtccag ctgtcccctt ttctgggact      60
attcaaggag gtctccagga cggacttcag atcactgtca atgggaccgt tctcagctcc     120
agtggaacca ggtttgctgt gaactttcag actggcttca gtggaaatga cattgccttc     180
cacttcaacc ctcggtttga agatggaggg tacgtggtgt gcaacacgag gcagaacgga     240 agctggggc cgaggagag gaagacacac atgcctttcc agaagggat gccctttgac        300 ctctgcttcc tggtgcagag ctcagatttc aaggtgatgg tgaacgggat cctcttcgtg     360

```
cagtacttcc accgcgtgcc cttccaccgt gtggacacca tctccgtcaa tggctctgtg    420
cagctgtcct acatcagctt ccagaacccc cgcacagtcc ctgttcagcc tgccttctcc    480
acggtgccgt tctcccagcc tgtctgtttc cacccaggc ccaggggcg cagacaaaaa      540 cctcccggcg tgtggcctgc aacccggct cccattaccc agacagtcat ccacacagtg    600
cagagcgccc ctggacagat gttctctact cccgccatcc cacctatgat gtaccccac    660 cccgcctatc cgatgccttt catcaccacc attctgggag gctgtaccc atccaagtcc    720 atcctcctgt caggcactgt cctgcccagt gctcagaggt tccacatcaa cctgtgctct    780
gggaaccaca tcgccttcca cctgaacccc cgttttgatg agaatgctgt ggtccgcaac    840
acccagatcg acaactcctg ggggtctgag agcgaagtc tgccccgaaa aatgcccttc    900
gtccgtggcc agagcttctc agtgtggatc ttgtgtgaag ctcactgcct caaggtggcc    960
gtggatggtc agcacctgtt tgaatactac catcgcctga ggaacctgcc caccatcaac   1020
agactggaag tgggggcga catccagctg acccatgtgc agacatag                  1068
```

<210> SEQ ID NO 14
<211> LENGTH: 355
<212> TYPE: PRT
<213> ORGANISM: Homo sapiens

<400> SEQUENCE: 14

```
Met Ala Phe Ser Gly Ser Gln Ala Pro Tyr Leu Ser Pro Ala Val Pro
 1               5                  10                  15

Phe Ser Gly Thr Ile Gln Gly Gly Leu Gln Asp Gly Leu Gln Ile Thr
                20                  25                  30

Val Asn Gly Thr Val Leu Ser Ser Gly Thr Arg Phe Ala Val Asn
            35                  40                  45

Phe Gln Thr Gly Phe Ser Gly Asn Asp Ile Ala Phe His Phe Asn Pro
        50                  55                  60

Arg Phe Glu Asp Gly Gly Tyr Val Val Cys Asn Thr Arg Gln Asn Gly
    65                  70                  75                  80

Ser Trp Gly Pro Glu Glu Arg Lys Thr His Met Pro Phe Gln Lys Gly
                    85                  90                  95

Met Pro Phe Asp Leu Cys Phe Leu Val Gln Ser Ser Asp Phe Lys Val
                100                 105                 110

Met Val Asn Gly Ile Leu Phe Val Gln Tyr Phe His Arg Val Pro Phe
            115                 120                 125

His Arg Val Asp Thr Ile Ser Val Asn Gly Ser Val Gln Leu Ser Tyr
        130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                    165                 170                 175

Arg Arg Gln Lys Pro Pro Gly Val Trp Pro Ala Asn Pro Ala Pro Ile
                180                 185                 190

Thr Gln Thr Val Ile His Thr Val Gln Ser Ala Pro Gly Gln Met Phe
            195                 200                 205

Ser Thr Pro Ala Ile Pro Pro Met Met Tyr Pro His Pro Ala Tyr Pro
        210                 215                 220

Met Pro Phe Ile Thr Thr Ile Leu Gly Gly Leu Tyr Pro Ser Lys Ser
225                 230                 235                 240

Ile Leu Leu Ser Gly Thr Val Leu Pro Ser Ala Gln Arg Phe His Ile
                    245                 250                 255
```

```
Asn Leu Cys Ser Gly Asn His Ile Ala Phe His Leu Asn Pro Arg Phe
            260                 265                 270

Asp Glu Asn Ala Val Val Arg Asn Thr Gln Ile Asp Asn Ser Trp Gly
        275                 280                 285

Ser Glu Glu Arg Ser Leu Pro Arg Lys Met Pro Phe Val Arg Gly Gln
    290                 295                 300

Ser Phe Ser Val Trp Ile Leu Cys Glu Ala His Cys Leu Lys Val Ala
305                 310                 315                 320

Val Asp Gly Gln His Leu Phe Glu Tyr Tyr His Arg Leu Arg Asn Leu
                325                 330                 335

Pro Thr Ile Asn Arg Leu Glu Val Gly Gly Asp Ile Gln Leu Thr His
            340                 345                 350

Val Gln Thr
        355

<210> SEQ ID NO 15
<211> LENGTH: 972
<212> TYPE: DNA
<213> ORGANISM: Homo sapiens

<400> SEQUENCE: 15
atggccttca gcggttccca ggctccctac ctgagtccag ctgtcccctt ttctgggact    60
attcaaggag gtctccagga cggacttcag atcactgtca atgggaccgt tctcagctcc   120
agtggaacca ggtttgctgt gaactttcag actggcttca gtggaaatga cattgccttc   180
cacttcaacc ctcggtttga agatggaggg tacgtggtgt gcaacacgag cagaacggaa   240 agctggggc cgaggagag gaagacacac atgccttcc agaagggat gccctttgac       300 ctctgcttcc tggtgcagag ctcagatttc aaggtgatgg tgaacgggat cctcttcgtg   360
cagtacttcc accgcgtgcc cttccaccgt gtggacacca tctccgtcaa tggctctgtg   420
cagctgtcct acatcagctt ccagcctccc ggcgtgtggc ctgccaaccc ggctcccatt   480
acccagacag tcatccacac agtgcagagc gccctggac agatgttctc tactcccgcc    540
atcccaccta tgatgtaccc caccccgcc tatccgatgc ctttcatcac caccattctg     600
ggagggctgt acccatccaa gtccatcctc ctgtcaggca ctgtcctgcc cagtgctcag   660
aggttccaca tcaacctgtg ctctgggaac acatcgcct tccacctgaa cccccgtttt   720
gatgagaatg ctgtggtccg caacacccag atcgacaact cctggggtc tgaggagcga     780 agtctgcccc gaaaaatgcc cttcgtccgt ggccagagct ctcagtgtg atcttgtgt      840 gaagctcact gcctcaaggt ggccgtggat ggtcagcacc tgtttgaata ctaccatcgc    900
ctgaggaacc tgcccaccat caacagactg gaagtggggg cgacatcca gctgacccat    960 gtgcagacat ag                                                       972

<210> SEQ ID NO 16
<211> LENGTH: 323
<212> TYPE: PRT
<213> ORGANISM: Homo sapiens

<400> SEQUENCE: 16

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
```

```
              35                  40                  45
Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Phe His Ile
    210                 215                 220

Asn Leu Cys Ser Gly Asn His Ile Ala Phe His Leu Asn Pro Arg Phe
225                 230                 235                 240

Asp Glu Asn Ala Val Val Arg Asn Thr Gln Ile Asp Asn Ser Trp Gly
                245                 250                 255

Ser Glu Glu Arg Ser Leu Pro Arg Lys Met Pro Phe Val Arg Gly Gln
            260                 265                 270

Ser Phe Ser Val Trp Ile Leu Cys Glu Ala His Cys Leu Lys Val Ala
        275                 280                 285

Val Asp Gly Gln His Leu Phe Glu Tyr Tyr His Arg Leu Arg Asn Leu
    290                 295                 300

Pro Thr Ile Asn Arg Leu Glu Val Gly Gly Asp Ile Gln Leu Thr His
305                 310                 315                 320

Val Gln Thr

<210> SEQ ID NO 17
<211> LENGTH: 1068
<212> TYPE: DNA
<213> ORGANISM: Homo sapiens

<400> SEQUENCE: 17
atggccttca gcggttccca ggctccctat ctgagcccag ccgtcccctt ttctgggact      60
atccaagggg gtctccagga cggatttcag atcactgtca atgggccgt tctcagctcc     120 agtggaacca ggtttgctgt ggactttcag acgggcttca gtggaaacga cattgccttc     180
cacttcaacc ctcggtttga agacggaggg tatgtggtgt gcaacacgag cagaaagga      240 agatggggc ccgaggagag gaagatgcac atgcccttcc agaagggat gccctttgac      300 ctctgcttcc tggtgcagag ctcagatttc aaggtgatgg tgaacgggag cctcttcgtg     360
cagtacttcc accgcgtgcc cttccaccgt gtggacacca tctccgtcaa tggctctgtg     420
cagctgtcct acatcagctt ccagaatccc cgcacagtcc ccgttcagcc tgccttctcc     480
```

-continued

```
acggtgccgt tctcccagcc tgtctgtttc ccacccaggc ccaggggggcg cagacaaaaa      540 cctcccagcg tgcggcctgc caacccagct cccattaccc agacagtcat ccacacggtg      600
cagagcgcct ctggacagat gttctctact cccgccatcc cacctatgat gtaccccccac     660 cctgcctatc cgatgccttt catcaccacc attccgggag ggctgtaccc atccaagtcc      720
atcatcctgt caggcactgt cctgcccagt gctcagaggt tccacatcaa cctgtgctct      780
gggagccaca tcgccttcca catgaacccc cgttttgatg agaatgctgt ggtccgtaac      840
acccagatca caactcttg ggggtctgag gagcgaagtc tgccccgaaa aatgcccttc       900
gtccgaggcc agagcttctc ggtgtggatc ttgtgtgaag ctcactgcct caaggtggcc      960
gtggatggtc agcacgtgtt tgaatactac catcgcctga ggaacctgcc caccatcaac     1020
aaactggaag tgggtggcga catccagctg acccacgtgc agacatag                  1068
```

<210> SEQ ID NO 18
<211> LENGTH: 355
<212> TYPE: PRT
<213> ORGANISM: Homo sapiens

<400> SEQUENCE: 18

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Phe Gln Ile Thr
                20                  25                  30

Val Asn Gly Ala Val Leu Ser Ser Gly Thr Arg Phe Ala Val Asp
            35                  40                  45

Phe Gln Thr Gly Phe Ser Gly Asn Asp Ile Ala Phe His Phe Asn Pro
        50                  55                  60

Arg Phe Glu Asp Gly Gly Tyr Val Val Cys Asn Thr Arg Gln Lys Gly
65                  70                  75                  80

Arg Trp Gly Pro Glu Glu Arg Lys Met His Met Pro Phe Gln Lys Gly
                85                  90                  95

Met Pro Phe Asp Leu Cys Phe Leu Val Gln Ser Ser Asp Phe Lys Val
                100                 105                 110

Met Val Asn Gly Ser Leu Phe Val Gln Tyr Phe His Arg Val Pro Phe
            115                 120                 125

His Arg Val Asp Thr Ile Ser Val Asn Gly Ser Val Gln Leu Ser Tyr
        130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                165                 170                 175

Arg Arg Gln Lys Pro Pro Ser Val Arg Pro Ala Asn Pro Ala Pro Ile
                180                 185                 190

Thr Gln Thr Val Ile His Thr Val Gln Ser Ala Ser Gly Gln Met Phe
            195                 200                 205

Ser Thr Pro Ala Ile Pro Pro Met Met Tyr Pro His Pro Ala Tyr Pro
        210                 215                 220

Met Pro Phe Ile Thr Thr Ile Pro Gly Gly Leu Tyr Pro Ser Lys Ser
225                 230                 235                 240

Ile Ile Leu Ser Gly Thr Val Leu Pro Ser Ala Gln Arg Phe His Ile
                245                 250                 255

Asn Leu Cys Ser Gly Ser His Ile Ala Phe His Met Asn Pro Arg Phe
            260                 265                 270

```
Asp Glu Asn Ala Val Val Arg Asn Thr Gln Ile Asn Asn Ser Trp Gly
            275                 280                 285

Ser Glu Glu Arg Ser Leu Pro Arg Lys Met Pro Phe Val Arg Gly Gln
290                 295                 300

Ser Phe Ser Val Trp Ile Leu Cys Glu Ala His Cys Leu Lys Val Ala
305                 310                 315                 320

Val Asp Gly Gln His Val Phe Glu Tyr Tyr His Arg Leu Arg Asn Leu
                325                 330                 335

Pro Thr Ile Asn Lys Leu Glu Val Gly Gly Asp Ile Gln Leu Thr His
            340                 345                 350

Val Gln Thr
        355

<210> SEQ ID NO 19
<211> LENGTH: 1071
<212> TYPE: DNA
<213> ORGANISM: Homo sapiens

<400> SEQUENCE: 19
atggccttca gcggttgcca ggctccctat ctgagcccag ccgtccccctt ttctgggact    60
atccaagggg gtctccagga cggatttcag atcactgtca atggggccgt tctcagctgc   120
agtggaacca ggtttgctgt ggactttcag acgggcttca gtggaaacga cattgccttc   180
cacttcaacc ctcggtttga agacggaggg tatgtggtgt gcaacacgag cagaaagga    240
acatgggggc cgaggagag gaagatgcac atgcccttcc agaagggat gccctttgac   300
ctctgcttcc tggtgcagag ctcagatttc aaggtgatgg tgaacgggag cctcttcgtg   360
cagtacttcc accgcgtgcc cttccaccgt gtggacacca tctccgtcaa tggctctgtg   420
cagctgtcct acatcagctt ccagaatccc gcgcagtcc ccgttcagcc tgccttctcc   480
acggtgccgt ctcccagcc tgtctgtttc ccacccaggc caggggggcg cagacaaaaa   540
cctcccagcg tgcggcctgc caacccagct cccattaccc agacagtcat ccacacggtg   600
cagagtgcct ctggacagat gttctctcag actcccgcca tcccacctat gatgtacccc   660
caccctgcct atccgatgcc tttcatcacc accattccgg gagggctgta cccatccaag   720
tccatcatcc tgtcaggcac tgtcctgccc agtgctcaga ggttccacat caacctgtgc   780
tctgggagcc acatcgcctt ccacatgaac ccccgttttg atgagaatgc cgtggtccgt   840
aacacccaga tcaacaactc ttgggggtct gaggagcgaa gtctgccccg aaaaatgccc   900
ttcgtccgag ccagagcttt ctcggtgtgg atcttgtgtg aagctcactg cctcaaggtg   960
gccgtggatg gtcagcacgt gtttgaatac taccatcgcc tgaggaacct gcccaccatc  1020
aacaaactgg aagtgggtgg cgacatccag ctgacccacg tgcagacata g            1071

<210> SEQ ID NO 20
<211> LENGTH: 356
<212> TYPE: PRT
<213> ORGANISM: Homo sapiens

<400> SEQUENCE: 20

Met Ala Phe Ser Gly Cys Gln Ala Pro Tyr Leu Ser Pro Ala Val Pro
1               5                   10                  15

Phe Ser Gly Thr Ile Gln Gly Gly Leu Gln Asp Gly Phe Gln Ile Thr
                20                  25                  30

Val Asn Gly Ala Val Leu Ser Cys Ser Gly Thr Arg Phe Ala Val Asp
            35                  40                  45
```

Phe Gln Thr Gly Phe Ser Gly Asn Asp Ile Ala Phe His Phe Asn Pro
 50                  55                  60

Arg Phe Glu Asp Gly Gly Tyr Val Val Cys Asn Thr Arg Gln Lys Gly
 65                  70                  75                  80

Thr Trp Gly Pro Glu Glu Arg Lys Met His Met Pro Phe Gln Lys Gly
                 85                  90                  95

Met Pro Phe Asp Leu Cys Phe Leu Val Gln Ser Ser Asp Phe Lys Val
                100                 105                 110

Met Val Asn Gly Ser Leu Phe Val Gln Tyr Phe His Arg Val Pro Phe
                115                 120                 125

His Arg Val Asp Thr Ile Ser Val Asn Gly Ser Val Gln Leu Ser Tyr
    130                 135                 140

Ile Ser Phe Gln Asn Pro Arg Ala Val Pro Val Gln Pro Ala Phe Ser
145                 150                 155                 160

Thr Val Pro Phe Ser Gln Pro Val Cys Phe Pro Arg Pro Arg Arg Gly
                165                 170                 175

Arg Arg Gln Lys Pro Pro Ser Val Arg Pro Ala Asn Pro Ala Pro Ile
                180                 185                 190

Thr Gln Thr Val Ile His Thr Val Gln Ser Ala Ser Gly Gln Met Phe
                195                 200                 205

Ser Gln Thr Pro Ala Ile Pro Pro Met Met Tyr Pro His Pro Ala Tyr
    210                 215                 220

Pro Met Pro Phe Ile Thr Thr Ile Pro Gly Gly Leu Tyr Pro Ser Lys
225                 230                 235                 240

Ser Ile Ile Leu Ser Gly Thr Val Leu Pro Ser Ala Gln Arg Phe His
                245                 250                 255

Ile Asn Leu Cys Ser Gly Ser His Ile Ala Phe His Met Asn Pro Arg
                260                 265                 270

Phe Asp Glu Asn Ala Val Val Arg Asn Thr Gln Ile Asn Asn Ser Trp
                275                 280                 285

Gly Ser Glu Glu Arg Ser Leu Pro Arg Lys Met Pro Phe Val Arg Gly
    290                 295                 300

Gln Ser Phe Ser Val Trp Ile Leu Cys Glu Ala His Cys Leu Lys Val
305                 310                 315                 320

Ala Val Asp Gly Gln His Val Phe Glu Tyr Tyr His Arg Leu Arg Asn
                325                 330                 335

Leu Pro Thr Ile Asn Lys Leu Glu Val Gly Gly Asp Ile Gln Leu Thr
                340                 345                 350

His Val Gln Thr
    355

<210> SEQ ID NO 21
<211> LENGTH: 1062
<212> TYPE: DNA
<213> ORGANISM: Mus musculus

<400> SEQUENCE: 21
atggctctct tcagtgccca gtctccatac attaacccga tcatcccctt tactggacca      60
atccaaggag gctgcagga gggacttcag gtgaccctcc aggggactac caagagtttt     120
gcacaaaggt ttgtggtgaa ctttcagaac agcttcaatg gaaatgacat tgccttccac     180
ttcaaccccc ggtttgagga aggagggtat gtggtttgca acacgaagca gaacggacag     240
tggggtcctg aggagagaaa gatgcagatg cccttccaga gggggatgcc ctttgagctt     300
tgcttcctgg tgcagaggtc agagttcaag gtgatggtga acaagaaatt ctttgtgcag     360

```
taccaacacc gcgtacccta ccacctcgtg gacaccatcg ctgtctccgg ctgcttgaag    420
ctgtccttta tcaccttcca gaactctgca gcccctgtcc agcatgtctt ctccacagtg    480
cagttctctc agccagtcca gttcccacgg acccctaagg ggcgcaaaca gaaaactcag    540
aactttcgtc ctgcccacca ggcacccatg gctcaaacta ccatccatat ggttcacagc    600 accctggac agatgttctc tactcctgga atccctcctg tggtgtaccc caccccagcc     660
tataccatac ctttctacac ccccattcca aatgggcttt acccgtccaa gtccatcatg    720
atatcaggca atgtcttgcc agatgctacg aggttccata tcaaccttcg ctgtggaggt    780
gacattgctt tccacctgaa ccccgtttc aatgagaatg ctgttgtccg aaacactcag     840
atcaacaact cctgggggca ggaagagcga agtctgcttg ggaggatgcc cttcagtcga    900
ggccagagct tctcggtgtg gatcatatgt gaaggtcact gcttcaaggt agctgtgaat    960
ggtcaacaca tgtgtgaata ttaccaccgc ctgaagaact tgcaggatat caacactcta   1020
gaagtggcgg gtgatatcca gctgacccac gtgcagacat ag                       1062
```

<210> SEQ ID NO 22
<211> LENGTH: 353
<212> TYPE: PRT
<213> ORGANISM: Mus musculus

<400> SEQUENCE: 22

```
Met Ala Leu Phe Ser Ala Gln Ser Pro Tyr Ile Asn Pro Ile Ile Pro
1               5                   10                  15

Phe Thr Gly Pro Ile Gln Gly Gly Leu Gln Glu Gly Leu Gln Val Thr
            20                  25                  30

Leu Gln Gly Thr Thr Lys Ser Phe Ala Gln Arg Phe Val Val Asn Phe
        35                  40                  45

Gln Asn Ser Phe Asn Gly Asn Asp Ile Ala Phe His Phe Asn Pro Arg
    50                  55                  60

Phe Glu Glu Gly Gly Tyr Val Val Cys Asn Thr Lys Gln Asn Gly Gln
65                  70                  75                  80

Trp Gly Pro Glu Glu Arg Lys Met Gln Met Pro Phe Gln Lys Gly Met
                85                  90                  95

Pro Phe Glu Leu Cys Phe Leu Val Gln Arg Ser Glu Phe Lys Val Met
            100                 105                 110

Val Asn Lys Lys Phe Phe Val Gln Tyr Gln His Arg Val Pro Tyr His
        115                 120                 125

Leu Val Asp Thr Ile Ala Val Ser Gly Cys Leu Lys Leu Ser Phe Ile
    130                 135                 140

Thr Phe Gln Asn Ser Ala Ala Pro Val Gln His Val Phe Ser Thr Val
145                 150                 155                 160

Gln Phe Ser Gln Pro Val Gln Phe Pro Arg Thr Pro Lys Gly Arg Lys
                165                 170                 175

Gln Lys Thr Gln Asn Phe Arg Pro Ala His Gln Ala Pro Met Ala Gln
            180                 185                 190

Thr Thr Ile His Met Val His Ser Thr Pro Gly Gln Met Phe Ser Thr
        195                 200                 205

Pro Gly Ile Pro Pro Val Val Tyr Pro Thr Pro Ala Tyr Thr Ile Pro
    210                 215                 220

Phe Tyr Thr Pro Ile Pro Asn Gly Leu Tyr Pro Ser Lys Ser Ile Met
225                 230                 235                 240

Ile Ser Gly Asn Val Leu Pro Asp Ala Thr Arg Phe His Ile Asn Leu
```

```
                 245                 250                 255
Arg Cys Gly Gly Asp Ile Ala Phe His Leu Asn Pro Arg Phe Asn Glu
            260                 265                 270

Asn Ala Val Val Arg Asn Thr Gln Ile Asn Asn Ser Trp Gly Gln Glu
        275                 280                 285

Glu Arg Ser Leu Leu Gly Arg Met Pro Phe Ser Arg Gly Gln Ser Phe
    290                 295                 300

Ser Val Trp Ile Ile Cys Glu Gly His Cys Phe Lys Val Ala Val Asn
305                 310                 315                 320

Gly Gln His Met Cys Glu Tyr Tyr His Arg Leu Lys Asn Leu Gln Asp
                325                 330                 335

Ile Asn Thr Leu Glu Val Ala Gly Asp Ile Gln Leu Thr His Val Gln
            340                 345                 350

Thr

<210> SEQ ID NO 23
<211> LENGTH: 969
<212> TYPE: DNA
<213> ORGANISM: Mus musculus

<400> SEQUENCE: 23
atggctctct tcagtgccca gtctccatac attaacccga tcatcccctt tactggacca      60
atccaaggag gctgcagga gggacttcag gtgaccctcc aggggactac caagagtttt     120
gcacaaaggt ttgtggtgaa ctttcagaac agcttcaatg aaatgacat tgccttccac     180
ttcaaccccc ggtttgagga aggagggtat gtggtttgca cacgaagca gaacggacag     240
tggggtcctg aggagagaaa gatgcagatg cccttccaga aggggatgcc ctttgagctt     300
tgcttcctgg tgcagaggtc agagttcaag gtgatggtga acaagaaatt ctttgtgcag     360
taccaacacc gcgtacccta ccacctcgtg gacaccatcg ctgtctccgg ctgcttgaag     420
ctgtcccttta tcaccttcca gactcagaac tttgtcctg cccaccaggc acccatggct     480
caaactacca tccatatggt tcacagcacc ctggacaga tgttctctac tcctggaatc     540
cctcctgtgg tgtaccccac cccagcctat accatacctt ctacaccccc attccaaat     600
gggctttacc cgtccaagtc catcatgata tcaggcaatg tcttgccaga tgctacgagg     660
ttccatatca accttcgctg tggaggtgac attgctttcc acctgaaccc cgtttcaat     720
gagaatgctg ttgtccgaaa cactcagatc aacaactcct gggggcagga agagcgaagt     780
ctgcttggga ggatgccctt cagtcgaggc cagagcttct cggtgtggat catatgtgaa     840
ggtcactgct tcaaggtagc tgtgaatggt caacacatgt gtgaatatta ccaccgcctg     900
aagaacttgc aggatatcaa cactctagaa gtggcgggtg atatccagct gacccacgtg     960
cagacatag                                                             969

<210> SEQ ID NO 24
<211> LENGTH: 322
<212> TYPE: PRT
<213> ORGANISM: Mus musculus

<400> SEQUENCE: 24

Met Ala Leu Phe Ser Ala Gln Ser Pro Tyr Ile Asn Pro Ile Ile Pro
1               5                   10                  15

Phe Thr Gly Pro Ile Gln Gly Gly Leu Gln Glu Gly Leu Gln Val Thr
            20                  25                  30

Leu Gln Gly Thr Thr Lys Ser Phe Ala Gln Arg Phe Val Val Asn Phe
```

```
            35                  40                  45
Gln Asn Ser Phe Asn Gly Asn Asp Ile Ala Phe His Phe Asn Pro Arg
     50                  55                  60

Phe Glu Glu Gly Gly Tyr Val Val Cys Asn Thr Lys Gln Asn Gly Gln
 65                  70                  75                  80

Trp Gly Pro Glu Glu Arg Lys Met Gln Met Pro Phe Gln Lys Gly Met
                 85                  90                  95

Pro Phe Glu Leu Cys Phe Leu Val Gln Arg Ser Glu Phe Lys Val Met
             100                 105                 110

Val Asn Lys Lys Phe Phe Val Gln Tyr Gln His Arg Val Pro Tyr His
         115                 120                 125

Leu Val Asp Thr Ile Ala Val Ser Gly Cys Leu Lys Leu Ser Phe Ile
     130                 135                 140

Thr Phe Gln Thr Gln Asn Phe Arg Pro Ala His Gln Ala Pro Met Ala
145                 150                 155                 160

Gln Thr Thr Ile His Met Val His Ser Thr Pro Gly Gln Met Phe Ser
                165                 170                 175

Thr Pro Gly Ile Pro Pro Val Val Tyr Pro Thr Pro Ala Tyr Thr Ile
            180                 185                 190

Pro Phe Tyr Thr Pro Ile Pro Asn Gly Leu Tyr Pro Ser Lys Ser Ile
        195                 200                 205

Met Ile Ser Gly Asn Val Leu Pro Asp Ala Thr Arg Phe His Ile Asn
    210                 215                 220

Leu Arg Cys Gly Gly Asp Ile Ala Phe His Leu Asn Pro Arg Phe Asn
225                 230                 235                 240

Glu Asn Ala Val Val Arg Asn Thr Gln Ile Asn Asn Ser Trp Gly Gln
                245                 250                 255

Glu Glu Arg Ser Leu Leu Gly Arg Met Pro Phe Ser Arg Gly Gln Ser
            260                 265                 270

Phe Ser Val Trp Ile Ile Cys Glu Gly His Cys Phe Lys Val Ala Val
        275                 280                 285

Asn Gly Gln His Met Cys Glu Tyr Tyr His Arg Leu Lys Asn Leu Gln
    290                 295                 300

Asp Ile Asn Thr Leu Glu Val Ala Gly Asp Ile Gln Leu Thr His Val
305                 310                 315                 320

Gln Thr

<210> SEQ ID NO 25
<211> LENGTH: 42
<212> TYPE: DNA
<213> ORGANISM: Artificial Sequence
<220> FEATURE:
<223> OTHER INFORMATION: /note="Description of Artificial Sequence:
      Gal-1 sense synthetic primer"

<400> SEQUENCE: 25
cgcgaacaga ttggaggtgc ttgtggtctg gtcgccagca ac                    42

<210> SEQ ID NO 26
<211> LENGTH: 42
<212> TYPE: DNA
<213> ORGANISM: Artificial Sequence
<220> FEATURE:
<223> OTHER INFORMATION: /note="Description of Artificial Sequence:
      Gal-1 antisense synthetic primer"

<400> SEQUENCE: 26
```

```
gtggcggccg ctctattagt caaaggccac acatttgatc tt                      42

<210> SEQ ID NO 27
<211> LENGTH: 42
<212> TYPE: DNA
<213> ORGANISM: Artificial Sequence
<220> FEATURE:
<223> OTHER INFORMATION: /note="Description of Artificial Sequence:
      Gal-3 sense synthetic primer"

<400> SEQUENCE: 27
cgcgaacaga ttggaggtgc agacaatttt tcgctccatg at                      42

<210> SEQ ID NO 28
<211> LENGTH: 43
<212> TYPE: DNA
<213> ORGANISM: Artificial Sequence
<220> FEATURE:
<223> OTHER INFORMATION: /note="Description of Artificial Sequence:
      Gal-3 antisense synthetic primer"

<400> SEQUENCE: 28
gtggcggccg ctctattagt atcatggtat atgaagcact ggt                     43
```

ANTI-GALECTIN ANTIBODY BIOMARKERS PREDICTIVE OF ANTI-IMMUNE CHECKPOINT AND ANTI-ANGIOGENESIS RESPONSES

CROSS-REFERENCE TO RELATED APPLICATIONS

This application claims the benefit of U.S. Provisional Application No. 62/074,779, filed on 4 Nov. 2014; the entire contents of said application are incorporated herein in their entirety by this reference.

BACKGROUND OF THE INVENTION

Cancer immune therapy is a rapidly developing field that has yielded impressive and promising breakthroughs. For example, CTLA-4 is an immune checkpoint molecule with immunosuppressive function (Korman et al. (2006) *Adv. Immunol.* 90:297-339). CTLA-4 ligation on activated T cells downregulates T cell responses, acting as the brakes on T cell activation. Clinical studies have shown that ipilimumab (Ipi), a fully humanized monoclonal antibody that blocks CTLA-4 activity, improves overall survival in a subset of patients with metastatic melanoma (Hodi et al. (2010) *N. Engl. J. Med.* 363:711-723; Robert et al. (2010) *N. Engl. J. Med.* 364:2517-2526). These studies have led FDA to approve Ipi for use in advanced melanoma patients. The limitation of Ipi is that only a relatively small proportion of patients achieve clinical responses. Combination of Ipi with other therapeutics is therefore needed to improve the efficacy of anti-CTLA4 therapy.

Recent studies have found that higher pre-treatment levels of pro-angiogenic growth factor VEGF-A, also known as VEGF, was associated with decreased survival in Ipi treated patients with metastatic melanoma (Yuan er al. (2014) *Cancer Immunol. Res.* 2:127-132), indicating that VEGF influences clinical outcomes to Ipi therapy. Indeed, it has been increasingly appreciated that angiogenesis has overlapping mechanisms with immune response (Terme et al. (2012) *Clin. Develop. Immunol.*, Article ID 492920). VEGF has profound effects on immune regulatory cell function. VEGF inhibits dendritic cell maturation and antigen presentation and promotes Treg and MDSC expansion in the tumor microenvironments (Ohm et al. (2001) *Immunol. Res.* 23:263-272; Oyama et al. (1998) *J. Immunol.* 160:1224-1232; Vanneman and Dranoff (2012) *Nat Rev. Cancer* 12:237-251). Increasing evidence also indicate a role for angiogenic factors in influencing lymphocyte trafficking across endothelia into tumor deposits (Kandalaft et al. (2011) *Curr. Top. Microbiol. Immunol.* 344:129-148). These findings support combination of Ipi with anti-VEGF for melanoma treatment. Indeed, a recent phase I study with metastatic melanoma has shown a synergistic clinical effect by addition of bevacizumab (Bev), a fully humanized monoclonal antibody that neutralizes VEGF, to Ipi (Hodi et al. (2014) *Cancer Immunol. Res.* 2:632-642). Pathological studies have shown that Ipi plus Bev (Ipi-Bev) enhanced infiltration of lymphocytes in tumors (Hodi et al. (2014) *Cancer Immunol. Res.* 2:632-642). Furthermore, Ipi-Bev increased memory effector T cells and levels of antibodies to galectin (Gal)-1, -3 and -9 in the peripheral blood of the patients (Hodi et al. (2014) *Cancer Immunol. Res.* 2:632-642).

While the combination of ipilimumab with anti-VEGF (e.g., bevacizumab) or PD-1 blockade increases clinical efficacy and response rate of ipilimumab, the best response rate thus far observed has been approximately 50% using ipilimumab in combination with PD-1 blockade. Reliable biomarkers that can predict response or resistance to anti-immune checkpoint and anti-angiogenesis combination therapies (e.g., immune checkpoint blockade, such as CTLA-4 inhibition, in combination with anti-angiogenesis blockade, such as VEGF inhibition) are therefore critical for stratifying patient populations and selecting patients who will or will not benefit from such immune therapies. However, such biomarkers are not currently known. Accordingly, there is a great need to identify such biomarkers useful for diagnostic, prognostic, and therapeutic purposes.

SUMMARY OF THE INVENTION

The present invention is based, at least in part, on the discovery that circulating anti-galectin antibodies (i.e., anti-Gal-1, anti-Gal-3, and/or anti-Gal-9 antibodies) are a highly specific early biomarker for prediction of clinical outcomes (e.g., poor clinical outcomes such as progressive disease and shortened survival) in cancer patients treated with a combination of anti-immune checkpoint and anti-angiogenesis therapies, such as those comprising an anti-CTLA-4 and anti-VEGF therapeutic (e.g., ipilimumab in combination with bevacizumab, and the like). Increased circulating anti-galectin antibodies (i.e., anti-Gal-1, anti-Gal-3, and/or anti-Gal-9 antibodies) is a mechanism for increased responsiveness to anti-cancer immunotherapy and adding or promoting anti-galectin antibodies (i.e., anti-Gal-1, anti-Gal-3, and/or anti-Gal-9 antibodies) is believed to improve the efficacy of anti-cancer therapies (e.g., immunotherapies) combining anti-immune checkpoint and anti-angiogenesis agents.

In one aspect, a method of identifying the likelihood of a cancer in a subject to be responsive to an anti-immune checkpoint and anti-angiogenesis combination therapy, the method comprising: a) obtaining or providing a patient sample from a patient having cancer; b) measuring the amount or activity of at least one antibody that specifically binds a biomarker listed in Table 1, or antigen-binding fragment thereof, in the subject sample; and c) comparing said amount or activity of the at least one antibody that specifically binds the biomarker listed in Table 1, or antigen-binding fragment thereof, in a control sample, wherein a significantly increased amount or activity of the at least one antibody that specifically binds the biomarker listed in Table 1, or antigen-binding fragment thereof, in the subject sample relative to the control sample identifies the cancer as being more likely to be responsive to the anti-immune checkpoint and anti-angiogenesis combination therapy and wherein a significantly decreased amount or activity of the at least one antibody that specifically binds the biomarker listed in Table 1, or antigen-binding fragment thereof, in the subject sample relative to the control sample identifies the cancer as being less likely to be responsive to the anti-immune checkpoint and anti-angiogenesis combination therapy, is provided.

In another aspect, a method of identifying a subject afflicted with a cancer as likely to be responsive to anti-immune checkpoint and anti-angiogenesis combination therapy, the method comprising: a) obtaining or providing a patient sample from a patient having cancer; b) measuring the amount or activity of at least one antibody that specifically binds a biomarker listed in Table 1, or antigen-binding fragment thereof, in the subject sample; and c) comparing said amount or activity of the at least one antibody that specifically binds the biomarker listed in Table 1, or antigen-binding fragment thereof, in a control sample, wherein a significantly increased amount or activity of the at least one antibody that specifically binds the biomarker listed in Table 1, or antigen-binding fragment thereof, in the subject sample relative to the control sample identifies the subject afflicted with the cancer as being more likely to be responsive to the anti-immune checkpoint and anti-angiogenesis combination therapy and wherein a significantly decreased amount or activity of the at least one antibody that specifically binds the biomarker listed in Table 1, or antigen-binding fragment thereof, in the subject sample relative to the control sample identifies the subject afflicted with the cancer as being less likely to be responsive to the anti-immune checkpoint and anti-angiogenesis combination therapy.

Numerous embodiments are further provided that can be applied to any aspect of the present invention described herein. For example, in one embodiment, the method further comprises recommending, prescribing, or administering anti-immune checkpoint and anti-angiogenesis combination therapy if the cancer or subject is determined likely to be responsive to anti-immune checkpoint and anti-angiogenesis combination therapy or administering anti-cancer therapy other than anti-immune checkpoint and anti-angiogenesis combination therapy if the cancer or subject is determined be less likely to be responsive to anti-immune checkpoint and anti-angiogenesis combination therapy. In another embodiment, the anti-cancer therapy is selected from the group consisting of targeted therapy, chemotherapy, radiation therapy, and/or hormonal therapy. In still another embodiment, the control sample is determined from a cancerous or non-cancerous sample from either the patient or a member of the same species to which the patient belongs. In yet another embodiment, the control sample is a cancerous or non-cancerous sample from the patient obtained from an earlier point in time than the patient sample, optionally wherein the control sample is obtained before the patient has received anti-immune checkpoint and anti-angiogenesis combination therapy and the patient sample is obtained after the patient has received anti-immune checkpoint and anti-angiogenesis combination therapy. In another embodiment, the control sample comprises cells or does not comprise cells. In still another embodiment, the control sample comprises cancer cells known to be responsive or non-responsive to the anti-immune checkpoint and anti-angiogenesis combination therapy.

In still another aspect, a method of assessing the efficacy of an agent for treating a cancer in a subject that is unlikely to be responsive to anti-immune checkpoint and anti-angiogenesis combination therapy, comprising: a) detecting the amount or activity of at least one antibody that specifically binds a biomarker listed in Table 1, or antigen-binding fragment thereof, from a subject in which the agent has not been administered; b) detecting the amount or activity of at least one antibody that specifically binds the biomarker listed in Table 1, or antigen-binding fragment thereof, in the subject in which the agent has been administered, and c) comparing the amount or activity of the at least one antibody that specifically binds the biomarker listed in Table 1, or antigen-binding fragment thereof, from steps a) and b), wherein a significantly increased amount or activity of the at least one antibody that specifically binds the biomarker listed in Table 1, or antigen-binding fragment thereof, in step b) relative to step a), indicates that the agent treats the cancer in the subject, is provided.

In yet another aspect, a method of assessing the efficacy of an anti-immune checkpoint and anti-angiogenesis combination therapy for treating a cancer in a subject or prognosing progression of a cancer treated with an anti-immune checkpoint and anti-angiogenesis combination therapy in a subject, comprising: a) detecting in a subject sample at a first point in time the amount or activity of at least one antibody that specifically binds a biomarker listed in Table 1, or antigen-binding fragment thereof; b) repeating step a) during at least one subsequent point in time after administration of the anti-immune checkpoint and anti-angiogenesis combination therapy; and c) comparing the expression and/or activity detected in steps a) and b), wherein a significantly increased amount or activity of the at least one antibody that specifically binds the biomarker listed in Table 1, or antigen-binding fragment thereof, in the at least one subsequent subject sample relative to the first subject sample, indicates that the cancer treated with an anti-immune checkpoint and anti-angiogenesis combination therapy is unlikely to progress or that the anti-immune checkpoint and anti-angiogenesis combination treats the cancer in the subject, is provided.

As described above, certain embodiments are applicable to any method described herein. For example, in one embodiment, the subject has undergone treatment, completed treatment, and/or is in remission for the cancer between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject.

In another aspect, a cell-based assay for screening for agents that have a cytotoxic or cytostatic effect on a cancer cell that is unresponsive to anti-immune checkpoint and anti-angiogenesis combination therapy comprising, contacting the cancer cell with a test agent, wherein the cancer cell is comprised within a B cell population, and determining the ability of the test agent to increase the amount or activity of at least one antibody that specifically binds a biomarker listed in Table 1, or antigen-binding fragment thereof, is provided. In one embodiment, the step of contacting occurs in vivo, ex vivo, or in vitro.

As described above, certain embodiments are applicable to any method described herein. For example, in one embodiment, the subject sample and/or the control sample has not been contacted with either a) any anti-cancer treatment, b) any anti-immune checkpoint agent, or c) any anti-angiogenesis agent. In another embodiment, the subject has not been administered any either a) any anti-cancer treatment, b) any anti-immune checkpoint agent, or c) any anti-angiogenesis agent. In still another embodiment, the method or assay further comprises recommending, prescribing, or administering at least one additional anti-cancer therapeutic agent, optionally wherein the at least one additional anti-cancer therapeutic agent is an anti-immune checkpoint agent, ipilimumab, an anti-angiogenesis agent, an anti-VEGF agent, bevacizumab, a neutralizing anti-Gal-1 antibody or antigen-binding fragment thereof, a neutralizing anti-Gal-3 antibody or antigen-binding fragment thereof, a neutralizing anti-Gal-9 antibody or antigen-binding fragment thereof, or combinations thereof. In yet another embodiment, the subject sample is selected from the group consisting of serum, whole blood, plasma, urine, cells, cell lines, and biopsies. In another embodiment, the amount of the least one antibody that specifically binds a biomarker listed in Table 1, or antigen-binding fragment thereof. In still another embodiment, the reagent is selected from the group consisting of a Gal-1 polypeptide or fragment thereof, Gal-3 polypeptide or fragment thereof, Gal-9 polypeptide or fragment thereof, or any combination thereof. In yet another embodiment, the at least one antibody that specifically binds a biomarker listed in Table 1, or antigen-binding fragment thereof, is assessed by enzyme-linked immunosorbent assay (ELISA), radioimmune assay (RIA), immunochemically, Western blot, or flow cytometry. In another embodiment, the biomarker listed in Table 1 is immobilized onto a solid support. In still another embodiment, the solid support is an array, bead, or plate. In yet another embodiment, the at least one antibody that specifically binds a biomarker listed in Table 1, or antigen-binding fragment thereof, is detected by detecting binding of an anti-IgG antibody against the antibody or antigen-binding fragment thereof. In another embodiment, the at least one antibody that specifically binds the biomarker listed in Table 1, or antigen-binding fragment thereof, is an anti-human Gal-1, an anti-human Gal-3, or an anti-human Gal-9 antibody, or an antigen-binding fragment thereof, optionally wherein the antibody or antigen-binding fragment thereof is a neutralizing antibody or neutralizing antigen-binding fragment thereof. In still another embodiment, the anti-immune checkpoint and anti-angiogenesis combination therapy comprises at least one antibody selected from the group consisting of anti-CTLA-4 antibodies, anti-PD-1 antibodies, anti-PD-L1 antibodies, anti-PD-L2 antibodies, anti-VEGF antibodies, and combinations thereof. In yet another embodiment, the anti-immune checkpoint therapy comprises ipilimumab and/or anti-angiogenesis therapy comprises bevacizumab. In another embodiment, the likelihood of the cancer in the subject to be responsive to anti-immune checkpoint and anti-angiogenesis combination therapy is the likelihood of at least one criteria selected from the group consisting of cellular proliferation, tumor burden, m-stage, metastasis, progressive disease, clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In still another embodiment, the cancer is a solid tumor. In yet another embodiment, the cancer is melanoma, non-small cell lung cancer (NSCLC), small cell lung cancer (SCLC), bladder cancer, prostate cancer, metastatic hormone-refractory prostate cancer, renal cell cancer, colon cancer, ovarian cancer, or brain glioblastoma multiforme. In another embodiment, the melanoma is metastatic melanoma. In still another embodiment, the subject is a mammal (e.g., an animal model of cancer or a human).

Figure 1:
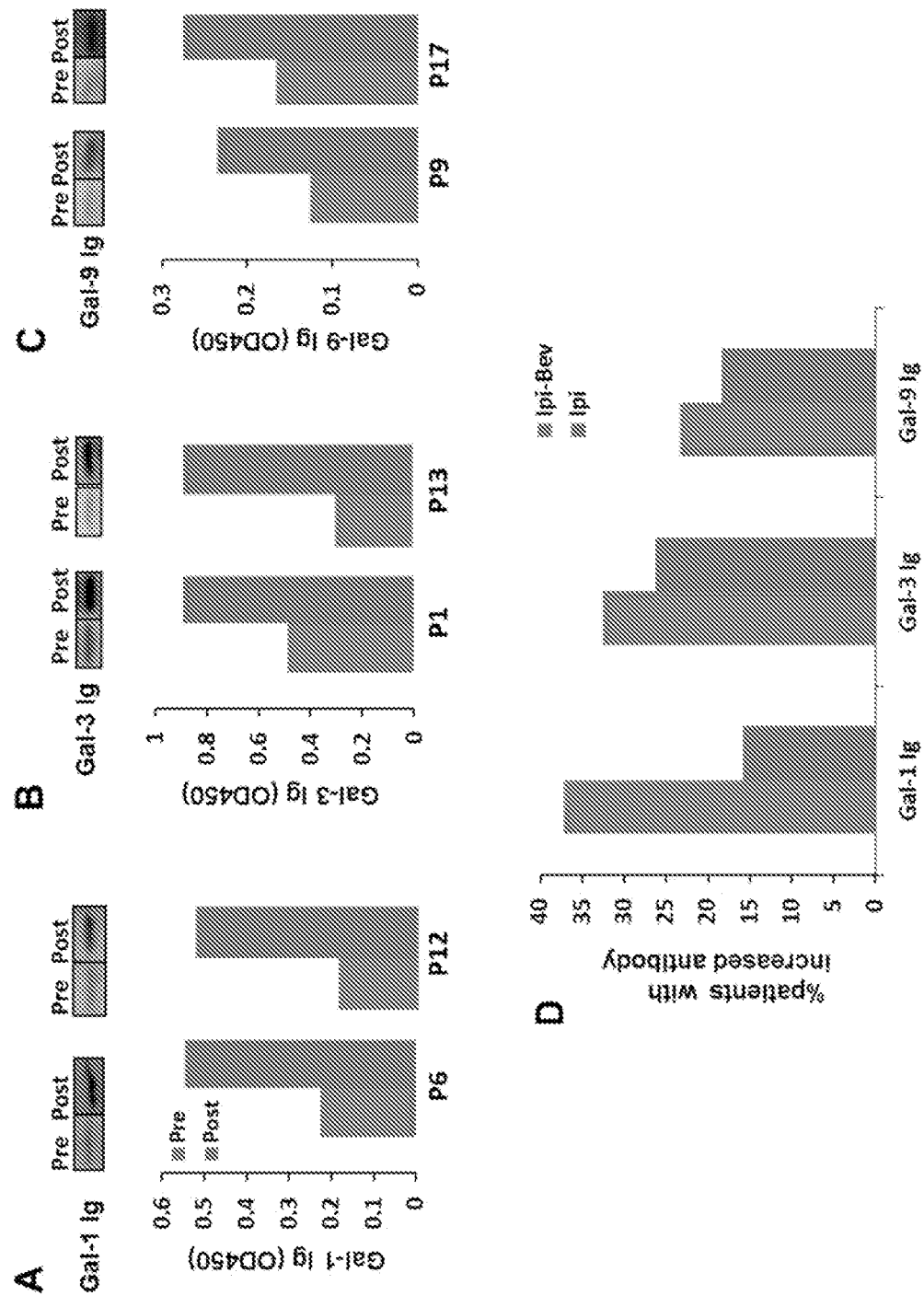
FIG. 1 includes 4 panels, identified as panels A, B, C, and D, which show that ipilimumab plus bevacizumab (Ipi-Bev) potentiates humoral immune response to Gal-1, -3 and -9 in metastatic melanoma patients. Panels A-C show anti-Gal-1, anti-Gal-3, and anti-Gal-9 antibody levels in pre- and post-treatment plasma samples of Ipi-Bev patients as determined by Western blot analysis (upper panels) and ELISA (lower panels), respectively. Results from representative patients (P1, P6, P9, P12, P13, and P17) are shown. Panel D shows the portions of Ipi-Bev and Ipi alone patients with increased humoral immune response to Gal-1 and Gal-3. Pre- and post-treatment plasma Gal-1 and Gal-3 Ig levels were evaluated using ELISA. Antibody levels were considered as increased when post-/pre-ratio is ≥1.45.

For any figure showing a bar histogram, curve, or other data associated with a legend, the bars, curve, or other data presented from left to right for each indication correspond directly and in order to the boxes from top to bottom of the legend. Similarly, for any figure showing survival curves based on percentage survival from 100% to 0%, the curves showing a higher percentage survival at the end of the measured time points correspond directly and in order to the labels from top to bottom of the legend.

DETAILED DESCRIPTION OF THE INVENTION

It has been determined herein that a humoral anti-Gal-1, Gal-3, and/or Gal-9 response is a specific biomarker for predicted clinical outcome in cancer patients (e.g., metastatic melanoma patients) receiving a combination of anti-immune checkpoint and anti-angiogenesis therapies (e.g., anti-CTLA-4 and anti-VEGF therapeutics, ipilimumab in combination with bevacizumab, and the like). Accordingly, the present invention relates, in part, to methods for stratifying patients and predicting response of a cancer in a subject to a combination of anti-immune checkpoint and anti-angiogenesis therapies based upon a determination and analysis of biomarkers described herein according to amount (e.g., copy number or level of expression) and/or activity, relative to a control. In addition, such analyses can be used in order to provide useful treatment regimens comprising a combination of anti-immune checkpoint and anti-angiogenesis therapies (e.g., based on predictions of clinical response, subject survival or relapse, timing of adjuvant or neoadjuvant treatment, etc.).

1. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

The term "angiogenesis" or "neovascularization" refers to the process by which new blood vessels develop from pre-existing vessels (Varner et al. (1999) *Angiogen.* 3:53-60; Mousa et al. (2000) *Angiogen. Stim. Inhib.* 35:42-44; Kim et al. (2000) *Amer. J. Path.* 156:1345-1362; Kim et al. (2000) *J. Biol. Chem.* 275:33920-33928; Kumar et al. (2000) Angiogenesis: From Molecular to Integrative Pharm. 169-180). Endothelial cells from pro-existing blood vessels or from circulating endothelial stem cells (Takahashi et al. (1995) *Nat. Med.* 5:434-438; Isner et al. (1999) *J. Clin. Invest.* 103:1231-1236) become activated to migrate, proliferate, and differentiate into structures with lumens, forming new blood vessels, in response to growth factor or hormonal cues, or hypoxic or ischemic conditions. During ischemia, such as occurs in cancer, the need to increase oxygenation and delivery of nutrients apparently induces the secretion of angiogenic factors by the affected tissue; these factors stimulate new blood vessel formation. Several additional terms are related to angiogenesis.

For example, the term "tissue exhibiting angiogenesis" refers to a tissue in which new blood vessels are developing from pre-existing blood vessels.

As used herein, the term "inhibiting angiogenesis," "diminishing angiogenesis," "reducing angiogenesis," and grammatical equivalents thereof refer to reducing the level of angiogenesis in a tissue to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control tissue, and most preferably is at the same level which is observed in a control tissue. A reduced level of angiogenesis need not, although it may, mean an absolute absence of angiogenesis. The invention does not require, and is not limited to, methods that wholly eliminate angiogenesis. The level of angiogenesis may be determined using methods well known in the art, including, without limitation, counting the number of blood vessels and/or the number of blood vessel branch points, as discussed herein and in the examples. An alternative in vitro assay contemplated includes the tubular cord formation assay that shows growth of new blood vessels at the cellular level [D. S. Grant et al., Cell, 58: 933-943 (1989)]. Artaccepted in vivo assays are also known, and involve the use of various test animals such as chickens, rats, mice, rabbits and the like. These in vivo assays include the chicken chorioallantoic membrane (CAM) assay, which is suitable for showing anti-angiogenic activity in both normal and neoplastic tissues (Ausprunk (1975) *Amer. J. Path.* 79:597-610 and Ossonowski and Reich (1980) *Cancer Res.* 30:2300-2309). Other in vivo assays include the mouse metastasis assay, which shows the ability of a compound to reduce the rate of growth of transplanted tumors in certain mice, or to inhibit the formation of tumors or preneoplastic cells in mice which are predisposed to cancer or which express chemically-induced cancer (Humphries et al. (1986) *Science* 233:467-470 and Humphries et al. (1988) *J. Clin. Invest.* 81:782-790). Moreover, in some embodiments, angiogenesis can be measured according to such attributes as pericyte maturation and vascular remodeling as described further herein.

Many anti-angiogenesis inhibitors are known in the art. Generally, such agents are disrupt angiogenesis to thereby be useful for treating cancer by either being (1) monoclonal antibodies directed against specific pro-angiogenic factors and/or their receptors (e.g., Avastin™, Erbitux™, Vectibix™, Herceptin™, and the like) or (2) small molecule tyrosine kinase inhibitors (TKIs) of multiple pro-angiogenic growth factor receptors (e.g., Tarveca™, Nexavar™, Suten™, and the like) or inhibitors of mTOR (mammalian target of rapamycin) (e.g., Torisel) or indirect anti-angiogenic agents such as Velcade™ and Celgene™. The first FDA-approved angiogenesis inhibitor, Bevacizumab (Abastin™, Genentech), a monoclonal antibody to vascular endothelial growth factor (VEGF), is approved as an anti-cancer agent, such as to treat metastatic colon cancer treatment in conjunction with standard conventional chemotherapy (see, for example U.S. Pat. No. 6,054,297). In one embodiment, the anti-angiogenesis agent is a VEGF inhibitor. The largest class of drugs that block angiogenesis are the multi-targeted tyrosine kinase inhibitors (TKIs) that target the VEGF receptor (VEGFR). These drugs such as sunitinib (Sutent™, Pfizer), sorafenib (Nexavar™, Bayer/Onyx Pharmaceuticals), and erlotinib (Tarveca™, Gennentech/OSI/Roche) have the advantages of hitting multiple targets, convenient oral administration, and cost effectiveness.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structre* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence, or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of anti-immune checkpoint and anti-angiogenesis combination therapy effects on a cancer. Biomarkers can include, without limitation, antibodies to proteins described herein, including those shown in Table 1, the Examples, and the Figures, as well as antigen-binding fragments thereof. Nucleic acids encoding same are also included within the term.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. In some embodiments, such cells exhibit such characteristics in part or in full due to the expression and activity of immune checkpoint proteins, such as PD-1, PD-L, and/or CTLA-4. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyclocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer encompasses melanoma. The term "melanoma" generally refers to cancers derived from melanocytes. Although melanocytes are predominantly located in skin, they are also found in other parts of the body, including the eye and bowel. Although cutaneous melanoma is most common, melanoma can originate from any melanocyte in the body. Though melanoma is less than five percent of the skin cancers, it is the seventh most common malignancy in the U.S. and is responsible for most of the skin cancer related deaths. The incidence has increased dramatically in the last several decades due to altered sun exposure habits of the population, several hereditary risk factors are also known. Other important risk factors are the number of pigment nevi, the number dysplastic nevi, and skin type. An increased risk is coupled to many nevi, both benign and dysplastic, and fair skin. Familial history of malignant melanomas is a risk factor, and approximately 8-12% of malignant melanoma cases are familial. Additional details are well known, such as described in US Pat. Publs. 2012-0269764 and 2013-0237445.

Malignant melanomas are clinically recognized based on the ABCD(E) system, where A stands for asymmetry, B for border irregularity, C for color variation, D for diameter >5 mm, and E for evolving. Further, an excision biopsy can be performed in order to corroborate a diagnosis using microscopic evaluation. Infiltrative malignant melanoma is traditionally divided into four principal histopathological subgroups: superficial spreading melanoma (SSM), nodular malignant melanoma (NMM), lentigo maligna melanoma (LMM), and aeral lentiginous melanoma (ALM). Other rare types also exists, such as desmoplastic malignant melanoma. A substantial subset of malignant melanomas appear to arise from melanocytic nevi and features of dysplastic nevi are often found in the vicinity of infiltrative melanomas. Melanoma is thought to arise through stages of progression from normal melanocytes or nevus cells through a dysplastic nevus stage and further to an in situ stage before becoming invasive. Some of the subtypes evolve through different phases of tumor progression, which are called radial growth phase (RGP) and vertical growth phase (VGP).

In a preferred embodiment, a melanoma subtype is melanoma resistant to treatment with inhibitors of BRAF and/or MEK. For example, the methods described herein are useful for diagnosing and/or prognosing melanoma subtypes that are resistant to treatment with inhibitors of BRAF and/or MEK. Inhibitors of BRAF and/or MEK, especially of mutant versions implicated in cancer (e.g., BRAF$^{V600E}$) are well-known in the art.

BRAF is a member of the Raf kinase family of serine/threonine-specific protein kinases. This protein plays a role in regulating the MAP kinase/ERKs signaling pathway, which affects cell division, differentiation, and secretion. BRAF transduces cellular regulatory signals from Ras to MEK in vivo. BRAF is also referred to as v-raf murine sarcoma viral oncogene homolog B1. BRAF mutants are a mutated form of BRAF that has increased basal kinase activity relative to the basal kinase activity of wild type BRAF is also an activated form of BRAF. More than 30 mutations of the BRAF gene that are associated with human cancers have been identified. The frequency of BRAF mutations in melanomas and nevi are 80%. In 90% of the cases, a Glu for Val substitution at position 600 (referred to as V600E) in the activation segment has been found in human cancers. This mutation is observed in papillary thyroid cancer, colorectal cancer and melanoma. Other mutations which have been found are R462I, I463S, G464E, G464V, G466A, G466E, G466V, G469A, G469E, N581S, E585K, D594V, F595L, G596R, L597V, T599I, V600D, V600K, V600R, K601E or A728V. Most of these mutations are clustered to two regions: the glycine-rich P loop of the N lobe and the activation segment and flanking regions. A mutated form of BRAF that induces focus formation more efficiently than wild type BRAF is also an activated form of BRAF. As used herein, the term "inhibitor of BRAF" refers to a compound or agent, such as a small molecule, that inhibits, decreases, lowers, or reduces the activity of BRAF or a mutant version thereof. Examples of inhibitors of BRAF include, but are not limited to, vemurafenib (PLX-4032; also known as RG7204, RO5185426, and vemurafenib, C23H18ClF2N3O3S), PLX 4720 (C17H14ClF2N3O3S), sorafenib (C21H16ClF3N4O3), GSK2118436, and the like. These and other inhibitors of BRAF, as well as non-limited examples of their methods of manufacture, are described in, for example, PCT Publication Nos. WO 2007/002325, WO 2007/002433, WO 2009/047505, WO 03/086467; WO 2009/143024, WO 2010/104945, WO 2010/104973, WO 2010/111527 and WO 2009/152087; U.S. Pat. Nos. 6,187, 799 and 7,329,670; and U.S. Patent Application Publication Nos. 2005/0176740 and 2009/0286783, each of which is herein incorporated by reference in its entirety).

MEK1 is a known as dual specificity mitogen-activated protein kinase 1, which is an enzyme that in human is encoded by the MAP2K1 gene. Mutations of MEK1 involved in cancer are known and include, for example, mutation selected from 59dclK and P387S or Q56P or C121S or P124L or F129L, and a MAP2K1 gene having a 175-177 AAG deletion or C1159T. As used herein, the term "inhibitor of MEK" refers to a compound or agent, such as a small molecule, that inhibits, decreases, lowers, or reduces the activity of MEK or a mutant version thereof. Examples of inhibitors of MEK include, but are not limited to, AZD6244 (6-(4-Bromo-2-chloro-phenylamino)-7-fluoro-3-methyl-3H-benzoimida-zole-5-carboxylic acid (2-hydroxy-ethoxy)-amide; selumetinib; Structure IV), and U0126 (1,4-diamino-2,3-dicyano-1,4-bis[2-aminophenylthio]butadiene; ARRY-142886; Structure V). Further non-limiting examples of MEK inhibitors include PD0325901, AZD2171, GDC-0973/XL-518, PD98059, PD184352, GSK1120212, RDEA436, RDEA119/BAY869766, AS703026, BIX 02188, BIX 02189, CI-1040 (PD184352), PD0325901, and PD98059. These and other inhibitors of MEK, as well as non-limiting examples of their methods of manufacture, are described in, for example, U.S. Pat. Nos. 5,525,625; 6,251, 943; 7,820,664; 6,809,106; 7,759,518; 7,485,643; 7,576, 072; 7,923,456; 7,732,616; 7,271,178; 7,429,667; 6,649, 640; 6,495,582; 7,001,905; US Patent Publication No. US2010/331334, US2009/0143389, US2008/0280957, US2007/0049591, US2011/0118298, International Patent Application Publication No. WO98/43960, WO99/01421, WO99/01426, WO00/41505, WO00/42002, WO00/42003, WO00/41994, WO00/42022, WO00/42029, WO00/68201, WO01/68619, WO02/06213 and WO03/077914, each of which is herein incorporated by reference in their entirety.

Malignant melanomas are staged according to the American Joint Committee on Cancer (AJCC) TNM-classification system, where Clark level is considered in T-classification. The T stage describes the local extent of the primary tumor, i.e., how far the tumor has invaded and imposed growth into surrounding tissues, whereas the N stage and M stage describe how the tumor has developed metastases, with the N stage describing spread of tumor to lymph nodes and the M stage describing growth of tumor in other distant organs. Early stages include: T0-1, N0, M0, representing localized tumors with negative lymph nodes. More advanced stages include: T2-4, N0, M0, localized tumors with more widespread growth and T1-4, N1-3, M0, tumors that have metastasized to lymph nodes and T1-4, N1-3, M1, tumors with a metastasis detected in a distant organ.

Stages I and II represent no metastatic disease and for stage I (T1a/b-2a,N0,M0) prognosis is very good. The 5-year survival for stage I disease is 90-95%, for stage II (T2b-4-b,N0,M0) the corresponding survival rate ranges from 80 to 45%. Stages III (T1a-4-b,N1a-3,M0) and IV (T(aII),N(aII),M1a-c) represent spread disease, and for these stages 5-year survival rates range from 70 to 24%, and from 19 to 7%, respectively. "Clark's level" is a measure of the layers of skin involved in a melanoma and is a melanoma prognostic factor. For example, level I involves the epidermis. Level II involves the epidermis and upper dermis. Level III involves the epidermis, upper dermis, and lower dermis. Level IV involves the epidermis, upper dermis, lower dermis, and subcutis. When the primary tumor has a thickness of >1 mm, ulceration, or Clark level IV-V, sentinel node biopsy (SNB) is typically performed. SNB is performed by identifying the first draining lymph node/s (i.e., the SN) from the tumor. This is normally done by injection of radiolabelled colloid particles in the area around the tumor, followed by injection of Vital Blue dye. Rather than dissection of all regional lymph nodes, which was the earlier standard procedure, only the sentinel nodes are generally removed and carefully examined. Following complete lymph node dissection is only performed in confirmed positive cases.

In addition to staging and diagnosis, factors like T-stage, Clark level, SNB status, Breslow's depth, ulceration, and the like can be used as endpoints and/or surrogates for analyses according to the present invention. For example, patients who are diagnosed at an advanced stage with metastases generally have a poor prognosis. For patients diagnosed with a localized disease, the thickness of the tumor measured in mm (Breslow) and ulceration can be endpoints for prognosis. Breslow's depth is determined by using an ocular micrometer at a right angle to the skin. The depth from the granular layer of the epidermis to the deepest point of invasion to which tumor cells have invaded the skin is directly measured. Clark level is important for thin lesions (<1 mm). Other prognostic factors include age, anatomic site of the primary tumor and gender. The sentinel node (SN) status can also be a prognostic factor, especially since the 5-year survival of SN-negative patients has been shown to be as high as 90%. Similarly, overall survival (OS) can be used as a standard primary endpoint. OS takes in to account time to death, irrespective of cause, e.g. if the death is due to cancer or not. Loss to follow-up is censored and regional recurrence, distant metastases, second primary malignant melanomas and second other primary cancers are ignored. Other surrogate endpoints for survival can be used, as described further herein, such as disease-free survival (DFS), which includes time to any event related to the same cancer, i.e. all cancer recurrences and deaths from the same cancer are events.

In addition to endpoints, certain diagnostic and prognostic markers can be analyzed in conjunction with the methods described herein. For example, lactate dehydrogenase (LDH) can be measured as a marker for disease progression. Patients with distant metastases and elevated LDH levels belong to stage IV M1c. Another serum biomarker of interest is S100B. High S100B levels are associated with disease progression, and a decrease in the S100B level is an indicator of treatment response. Melanoma-inhibiting activity (MIA) is yet another serum biomarker that has been evaluated regarding its prognostic value. Studies have shown that elevated MIA levels are rare in stage I and II disease, whereas in stage III or IV, elevation in MIA levels can be seen in 60-100% of cases. Addition useful biomarkers include RGS1 (associated with reduced relapse-free survival (RFS)), osteopontin (associated with both reduced RFS and disease-specific survival (DSS), and predictive of SLN metastases), HER3 (associated with reduced survival), and NCOA3 (associated with poor RFS and DSS, and predictive of SLN metastases). In addition, HMB-45, Ki-67 (M1B1), M1TF and MART-1/Melan-A or combinations of any described marker may be used for staining (Ivan & Prieto, 2010, Future Oncol. 6(7), 1163-1175; Linos et al., 2011, Biomarkers Med. 5(3) 333-360). In a literature review Rothberg et al. report that melanoma cell adhesion molecule (MCAM)/MUC18, matrix metalloproteinase-2, Ki-67, proliferating cell nuclear antigen (PCNA) and p16/INK4A are predictive of either all-cause mortality or melanoma specific mortality (Rothberg et al., 2009 J. Nat. Canc. Inst. 101(7) 452-474).

Currently, the typical primary treatment of malignant melanoma is radical surgery. Even though survival rates are high after excision of the primary tumor, melanomas tend to metastasize relatively early, and for patients with metastatic melanoma the prognosis is poor, with a 5-year survival rate of less than 10%. Radical removal of distant metastases with surgery can be an option and systemic chemotherapy can be applied, but response rates are normally low (in most cases less than 20%), and most treatment regiments fail to prolong overall survival. The first FDA-approved chemotherapeutic agent for treatment of metastatic melanoma was dacarbazine (DTIC), which can give response rates of approximately 20%, but where less than 5% may be complete responses. Temozolamid is an analog of DTIC that has the advantage of oral administration, and which have been shown to give a similar response as DTIC. Other chemotherapeutic agents, for example different nitrosureas, cisplatin, carboplatin, and vinca alkaloids, have been used, but without any increase in response rates. Since chemotherapy is an inefficient treatment method, immunotherapy agents have also been proposed. Most studied are interferon-alpha and interleukin-2. As single agents they have not been shown to give a better response than conventional treatment, but in combination with chemotherapeutic agents higher response rates have been reported. For patients with resected stage IIB or III melanoma, some studies have shown that adjuvant interferon alfa has led to longer disease free survival. For first- or second-line stage III and IV melanoma systemic treatments include: carboplatin, cisplatin, dacarbazine, interferon alfa, high-dose interleukin-2, paclitaxel, temozolomide, vinblastine or combinations thereof (NCCN Guidelines, ME-D, MS-9-13). Recently, the FDA approved Zelboraf™ (vemurafenib, also known as INN, PLX4032, RG7204 or R05185426) for unresectable or metastatic melanoma with the BRAF V600E mutation (Bollag et al. (2010) Nature 467:596-599 and Chapman et al. (2011) New Eng. J. Med. 364:2507-2516). Another recently approved drug for unresectable or metastatic melanoma is Yervoy® (ipilimumab) an antibody which binds to cytotoxic T-lymphocyte-associated antigen 4 (CTLA-4) (Hodi et al. (2010) New Eng. J. Med. 363:711-723). Others recently reported that patients with KIT receptor activating mutations or over-expression responded to Gleecvac® (imatinib mesylate) (Carvajal et al. (2011) JAMA 305:2327-2334). In addition, radiation treatment may be given as an adjuvant after removal of lymphatic metastases, but malignant melanomas are relatively radioresistant. Radiation treatment might also be used as palliative treatment. Melanoma oncologists have also noted that BRAF mutations are common in both primary and metastatic melanomas and that these mutations are reported to be present in 50-70% of all melanomas. This has led to an interest in B-raf inhibitors, such as Sorafenib, as therapeutic agents.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunotherapy that generally increases immune responses against the cancer (e.g., anti-immune checkpoint therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of two or more coordinately expressed biomarkers. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

The term "galectins" refers to family of carbohydrate binding proteins with affinity for β-galactosides, such as N-acetyllactosamine (Galβ1-3GlcNAc or Galβ1-4GlcNAc) (Rabinovich et al. (2007) *Scand. J. Immunol.* 66:143). In mammals, the galectin family includes 15 members, divided in 3 different groups according to the number of carbohydrate recognition domains (CRD). The CRD is a beta-sheet represented by approximately 135 amino acids, wherein 6 strands from a concave face and 5 strands form a convex face such that the concave face forms a groove for a β-galactoside, up to approximately a linear tetrasaccharide, to bind (Lobsanov et al. (1993) *J. Biol. Chem.* 268:27034-27038). Galectin-1, -2, -5, -7, -10, -11, -13, -14, and -15 are dimeric galectins that have two identical galectin subunits resulting from homodimerization. By contrast, galectin-4, -5, -8, -9, and -12 are tandem galectins because they maintain at least two distinct CRDs in the same polypeptide linked by a peptide domain. Finally, galectin-3 has a single CRD and a long, non-lectin domain that can form various structures, such as a pentamer or a monomer (Liu et al. (2010) *Annal. N.Y. Acad. Sci.* 1183:158-182). Most galectins exist in monomeric and non-covalent multimeric forms, secreted by a non-classical pathway that resembles the Na+/K+-ATPase pump (Hughes (2001) *Biochimie,* 83:667); Nickel (2005) *Traffic* 6:607). Only Gal-1, 2, 3, 4, 7, 8, 9, 10, 12, and 13 are known in humans.

Galectin-1, -3, and -9 are specific galectin family members that are well known to promote tumor growth and progression through various mechanisms, including promoting tumor growth, invasion/metastasis, and immune inhibition. Gal-1 and Gal-3 induce T cell apoptosis by binding to CD45 and inhibit T cell proliferation by blocking clustering of CD4/CD8 with CD45. Gal-9 inhibits immunity by inducing T cell apoptosis and inhibiting T cell proliferation and cytokine production via binding to Tim-3 on T cells. Emerging findings support Gal-1, -3 and -9 as key targets for cancer therapy.

Sequences, structures, domains, biophysical characteristics, and functions of Gal-1 gene and gene products have been described in the art. See, for example, Rabinovich et al. (2002) *Trends Immunol.* 23:313-320; Liu and Rabinovich (2005) *Nat. Rev. Cancer* 5:29-41; Rubinstein et al. (2004) *Cancer Cell* 5:241-251; Le et al. (200)5) *J. Clin. Oncol.* 23:8932-8941; Vasta et al. (2004) *Curr. Opin. Struct. Biol.* 14:617-630; Toscano et al. (2007) *Cyt. Growth Fact. Rev.* 18:57-71; Camby et al. (2006) *Glycobiol.* 16:137R-157R; U.S. Pat. Publs. 2003-0004132, 2003-0109464, 2006-0189514, 2009-0176223, 2009-0191182, 2012-0028825, and 2013-0011409, each of which is incorporated herein, by reference, in its entirety. Human Gal-1 in its monomeric form is a 14.3 kDa protein, encoded by the LSGALS1 gene located on chromosome 22q12. The full-length gene product is comprised of the splicing of four exons and encodes a 135 amino acid protein with a single carbohydrate recognition domain (CRD) specific for binding to glycoconjugates bearing N-acetyllactosamine (LacNAc) Type 1 (Galβ1-3GlcNAc) or Type 2 (Galβ1-4GlcNAc) disaccharides, with increased avidity for poly-LacNAc chains (Schwarz et al. (1998) *Biochem.* 37:5867). The nucleic acid and amino acid sequences of a representative human Gal-1 biomarker is available to the public at the GenBank database under NM_002305.3 and NP_002296.1. Nucleic acid and polypeptide sequences of Gal-1 orthologs in organisms other than humans are well known and include, for example, monkey Gal-1 (NM_001168627.1 and NP_001162098.1), chimpanzee Gal-1 (XM_003953882.1 and XP_003953931.1; XM_003953883.1 and XP_003953932.1; XM_001162104.3 and XP_001162104.1), mouse Gal-1 (NM_008495.1 and NP_032521.1), rat Gal-1 (NM_019904.1 and NP_063969.1), dog Gal-1 (NM_001201488.1 and NP_001188417.1), chicken Gal-1 (NM_206905.1 and NP_996788.1), and cow Gal-1 (NM_175782.1 and NP_786976.1), all of which are incorporated by reference into Table 1. For example, relevant Gal1 sequences useful for detection include those listed below in Table 1. Anti-Gal-1 antibodies suitable for detecting Gal-1 protein are well-known in the art and include, for example, BML-GA1161 (Enzo Life Sciences), 10871-05011 and 10871-0521 (AssayPro), PA5-25649 and PAS-19206 (Thermo Fischer Scientific, Inc.), LS-C125647 and LS-C23787) (Lifespan Biosciences), orb29058, orb20373, and orb10685 (Biorbyt), OAAB07343, OAEB01591, and OAAB03153 (Aviva Systems Biology), MAB5854 and AF5854 (R&D Systems), HPA049864 (Atlas Antibodies), and 11858-1-AP (Proteintech Group). It is to be noted that the term can further be used to refer to any combination of features described herein regarding Gal-1 molecules. For example, any combination of sequence composition, percentage identify, sequence length, domain structure, functional activity, etc. can be used to describe a Gal-1 molecule of the present invention.

Sequences, structures, domains, biophysical characteristics, and functions of Gal-3 gene and gene products have been described in the art (see, for example, Cherayil et al. (1990) *Proc. Natl. Acad. Sci. U.S.A.* 87:7324-7328; Gitt and Barondes (1991) *Biochem.* 30:82-89; Raz et al. (1991) *Cancer Res.* 51:2173-2178; Raimond et al. (1997) *Mamm. Genome* 8:706-707; Berbis et al. (2014) *Biochem. Biophys. Res. Commun.* 443:126-131). At least two transcript variants and isoforms of human Gal-3 are known. Transcript variant 1 (NM_002306.3) encodes long isoform 1 (NP_002297.2), whereas transcript variant 2 (NM_001177388.1) uses an alternative splie site in the 3' coding region, which causes a frameshift and encodes an isoform 2 (NP_001170859.1), which has a shorter and distinct C-terminus relative to isoform 1. Nucleic acid and polypeptide sequences of Gal-3 orthologs in organisms other than humans are well known and include, for example, monkey Gal-3 (NM_001266363.1 and NP_001253292.1), chimpanzee Gal-3 (XM_001148424.3 and XP_001148424.2), mouse Gal-3 (NM_001145953.1, NP_001139425.1, NM_010705.3, and NP_034835.1), rat Gal-3 (NM_031832.1 and NP_114020.1), dog Gal-3 (NM_001197043.1 and NP_001183972.1), chicken Gal-3 (NM_214591.1 and NP_999756.1), and cow Gal-3 (NM_001102341.2 and NP_001095811.1), all of which are incorporated by reference into Table 1. For example, relevant Gal-3 sequences useful for detection include those listed below in Table 1. Anti-Gal-3 antibodies suitable for detecting Gal-3 protein are well-known in the art and include, for example, orb128279, orb29909, orb48075, and orb27797 (Biorbyt), ALX-804-284 (Enzo Life Sciences), 130-101-312, and 130-101-315 (Miltenyi Biotec), 14979-1-AP and 60207-1-Ig (Proteintech Group), AHP2071, MCA4063Z, and AHP1481B (AbD Serotec). EB10775 (Everest Biotech), MA1-940, MA5-12367, PA5-34912, and PA5-34819 (Thermo Fisher Scientific), and HPA003162 (Atlas Antibodies). It is to be noted that the term can further be used to refer to any combination of features described herein regarding Gal-3 molecules. For example, any combination of sequence composition, percentage identify, sequence length, domain structure, functional activity, etc. can be used to describe a Gal-3 molecule of the present invention.

Sequences, structures, domains, biophysical characteristics, and functions of Gal-9 gene and gene products have been described in the art (see, for example, Tureci et al. (1997) *J. Biol. Chem.* 272:6416-6422; Matsumoto et al. (1998) *J. Biol. Chem.* 273:16976-16984; Matsumoto et al. (2002) *J. Immunol.* 168:1961-1967, Kageshita et al. (2002) *Int. J. Cancer* 99:809-816; Heusschen et al. (2014) *Biochem. Biophys. Acta* 1842:284-292; Sato et al. (2002) *Glycobiol.* 12:191-197; Park et al. (2002) *Genome Res.* 12:729-738). Several loci on human chromosome 17p encode variants of human Gal-9. For example, at least two transcript variants and isoforms of human Gal-9A are known. Transcript variant 1 (NM_009587.2) encodes the long isoform 1 of Gal-9A (NP_033665.1). By contrast, transcript variant 2 (NM_002308.3) lacks an internal, in-frame coding exon relative to transcript variant 1 resulting a shorter isoform 2 of Gal-9A (NP_0.002299.2) missing a 32 amino acid protein segment. Human Gal-9B was initially thought to represent a pseudogene, but is protein-encoding and is more centromeric than the similar Gal-9A locus on human chromosome 17p. Human Gal-9B sequences are publicly available as NM_1042685.1 and NP_001036150.1. Similarly, human Gal-9C sequences are publicly available as NM_001040078.2 and NP_001035167.2. Nucleic acid and polypeptide sequences of Gal-9 orthologs in organisms other than humans are well known and include, for example, mouse Gal-9 (NM_010708.2. NP_034838.2, NM_001159301.1, and NP_001152773.1), rat Gal-9 (NM_012977.1 and NP_037109.1), dog Gal-9 (NM_001003345.1 and NP_001003345.1), and cow Gal-9 (NM_001039177.2, NP_001034266.1, NM_001015570.3, and NP_001015570.1), all of which are incorporated by reference into Table 1. For example, relevant Gal-9 sequences useful for detection include those listed below in Table 1. Anti-Gal-9 antibodies suitable for detecting Gal-9 protein are well-known in the art and include, for example, 130-102-236, 120-102-217, and 130-105-160 (Miltenyi Biotec), PA5-29823 and PAS-32252 (Thermo Fisher Scientific), orb11543, orb95172, orb161114, and orb16471 (Biorbyt), LS-B6275, LS-C146970. LS-C81943, and LS-C300127 (Lifespan Biosciences), 50-9116-41 (eBioscience). HPA047218 (Atlas Antibodies), AF3535 and MAB3535 (R&D Systems), OAAF03042, OAAB11184, and ARP54821_P050 (Aviva Systems Biology), and 17938-1-AP (Proteintech Group). Anti-Gal-9B antibodies for detection Gal-9B protein are also well-known in the art and include, for example, PA5-23573 (Thermo Fisher Scientific), LS-C305017 and LS-C261850 (Lifespan Biosciences), OAAB00068 (Aviva Systems Biology), orb27913, orb189220, and orb184906 (Biorbyt), STJ40607 (St. John's Laboratory). AP52471PU-N (Acris Antibodies), HPA-46876 (Atlas Antibodies), MBS2003379 (MyBioSource), and AP10065c (Abgent). Similarly, anti-Gal-9C antibodies suitable for detecting Gal-9C protein are well-known in the art and include, for example, LS-C294015, LS-C301358, LS-C294014, and LS-C304031 (Lifespan Biosciences), sc-292682 (Santa Cruz Biotechnology), PAV236Hu02, PAV236Hu01, and PAV236Hu71 (Cloud-Clone Corporation), orb1189221 and orb184907 (Biorbyt), ARP70764_P050 (Aviva Systems Biology), 140398 and 140399 (United States Biological), and ab178351 (Abcam). It is to be noted that the term can further be used to refer to any combination of features described herein regarding Gal-9 molecules. For example, any combination of sequence composition, percentage identify, sequence length, domain structure, functional activity, etc. can be used to describe a Gal-9 molecule of the present invention.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATT-GCC-3' and a region having the nucleotide sequence 5'-TATGGC-3' share 50/o homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, HHLA2, butyrophilins, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and anti-CTLA-4 antibodies, either alone or in combination, are used to inhibit immune checkpoints.

"Ipilimumab" is a representative example of an anti-immune checkpoint therapy. Ipilimumab (previously MDX-010; Medarex Inc., marketed by Bristol-Myers Squibb as YERVOY™) is a fully human anti-human CTLA-4 monoclonal antibody that blocks the binding of CTLA-4 to CD80 and CD86 expressed on antigen presenting cells, thereby, blocking the negative down-regulation of the immune responses elicited by the interaction of these molecules (see, for example, WO 2013/169971, U.S. Pat. Publ. 2002/0086014, and U.S. Pat. Publ. 2003/0086930.

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% V of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term"isotype" refers to the antibody class (e.g., IgM or IgG 1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as anti-immune checkpoint inhibitor and anti-angiogenesis combination therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to anti-immune checkpoint and anti-angiogenesis combination treatment (e.g., therapeutic antibodies against CTLA-4, PD-L, PD-L1, VEGF, and the like). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer, (3) its absolute or relatively modulated presence or absence in clinical subset of patients with cancer (e.g., those responding to a particular anti-immune checkpoint and anti-angiogenesis combination therapy or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

The terms "prevent" "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to anti-immune checkpoint and anti-angiogenesis combination therapy" relates to any response of the hyperproliferative disorder (e.g., cancer) to an anti-immune checkpoint and anti-angiogenesis combination therapy, such as anti-CTLA4 and anti-VEGF therapy, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to rumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, anti-angiogenesis, chemotherapeutic, and/or radiation therapy). In some embodiments, normal cells are not affected to an extent that causes the normal cells to be unduly injured by the anti-immune checkpoint and anti-angiogenesis combination therapy. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L., Cancer Res 1982; 42: 2159-2164), cell death assays (Weisenthal L M, Shoemaker R H, Marsden J A, Dill P L, Baker J A, Moran E M, Cancer Res 1984: 94: 161-173; Weisenthal L M, Lippman M E, Cancer Treat Rep 1985: 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human Gal-1, Gal-3, and/or Gal-9 as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

The term "synergistic effect" refers to the combined effect of two or more anti-immune checkpoint and/or anti-angiogenesis agents can be greater than the sum of the separate effects of the anticancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see. e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence), metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit % risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) *Science* 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

GENETIC CODE

| | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |

-continued

GENETIC CODE

| | |
|---|---|
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Set, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Table 1) are well known in the art and readily available on publicly available databases, such as the National Center for Biotechnology Information (NCBI). For example, exemplary nucleic acid and amino acid sequences derived from publicly available sequence databases are provided below.

TABLE 1

SEQ ID NO: 1 Human Gal1 cDNA Sequence
  1    atggcttgtg gtctggtcgc ragcaacctg aatctcaaac ctggagagtg ccttcgagtg 61    cgaggcgagg tggctcctga cgctaagagc ttcgtgctga acctgggcaa agacagcaac 121    aacctgtgcc tgcacttcaa ccctcgcttc aacgcccacg gcgacgccaa caccatcgtg TABLE 1-continued

```
181    tgcaacagca aggacggcgg ggcctggggg accgagcagc gggaggctgt ctttcccttc 241    cagcctggaa gtgttgcaga ggtgtgcatc accttcgacc aggccaacct gaccgtcaag 301    ctgccagatg gatacgaatt caagttcccc aaccgcctca acctggaggc catcaactac 361    atggcagctg acggtgactt caagatcaaa tgtgtggcct ttgactga SEQ ID NO: 2 Human Gal1 Amino Acid Sequence
  1    macglvasnl nlkpgeclrv rgevapdaks fvlnlgkdsn nlclhfnprf nahgdantiv 61    cnskdggawg teqreavfpf qpgsvaevci tfdqanltvk lpdgyefkfp nrlnleainy 121    maadgdfkik cvafd SEQ ID NO: 3 Mouse Gal1 cDNA Sequence
  1    atggcctgtg gtctggtcgc cagcaacctg aatctcaaac ctggggaatg tctcaaagtt 61    cggggagagg tggcctcgga cgccaagagc tttgtgctga acccgggaaa agacagcaac 121    aacctgtgcc tacacttcaa tcctcgcttc aatgcccatg gagacgccaa caccattgtg 181    tgtaacacca aggaagatgg gacctgggga accgaacacc gggaacctgc cttccccttc 241    cagcccggga gcatcacaga ggtgtgcatc acctttgacc aggctgacct gaccatcaag 301    ctgccagacg gacatgaatt caagttcccc aaccgcctca acatggaggc catcaactac 361    atggcggcgg atggagactt caagattaag tgcgtggcct ttgagtga SEQ ID NO: 4 Mouse Gal1 Amino Acid Sequence
  1    macglvasnl nlkpgeclkv rgevasdaks fvlnlgkdsn nlclhfnprf nahgdantiv 61    cntkedgtwg tehrepafpf qpgsitevci tfdqadltik lpdghefkfp nrlnmeainy 121    maadgdfkik cvafe SEQ ID NO: 5 Human Gal-3 cDNA Sequence (transcript variant 1)
  1    atggcagaca attttcgct ccatgatgcg ttatctgggt ctggaaaccc aaaccctcaa 61    ggatggcctg gcgcatgggg gaaccagcct gctggggcag gggctaccc aggggcttcc 121    tatcctgggg cctaccccgg gcaggcaccc caggggctt atcctggaca gcacctcca 181    ggcgcctacc ctggagcacc tggagcttat cccggagcac ctgcacctgg agtctaccca 241    gggccaccca gcggccctgg gcctacccca tcttctggac agccaagtgc caccggagcc 301    taccctgcca ctggccccta tggcgcccct gctgggccac tgattgtgcc ttataacctg 361    cctttgcctg gggagtggt gcctcgcatg ctgataacaa ttctgggcac ggtgaagccc 421    aatgcaaaca gaattgcttt agatttccaa agagggaatg atgttgcctt ccactttaac 481    ccacgcttca atgagaacaa caggagagtc attgtttgca atacaaagct ggataataac 541    tggggaaggg aagaaagaca gtcggttttc ccatttgaaa gtgggaaacc attcaaaata 601    caagtactgg ttgaacctga ccacttcaag gttgcagtga atgatgctca cttgttgcag 661    tacaatcatc gggttaaaaa actcaatgaa atcagcaaac tgggaatttc tggtgacata 721    gacctcacca gtgcttcata taccatgata taa SEQ ID NO: 6 Human Gal-3 Amino Acid Sequence (isoform 1)
  1    madnfslhda lsgsgnpnpq gwpgawgnqp agaggypgas ypgaypgqap pgaypgqapp 61    gaypgapgay pgapapgvyp gppsgpgayp ssgqpsatga ypatgpygap agplivpynl 121    plpggvvprm litilgtvkp nanrialdfq rgndvafhfn prfnennrrv ivcntkldnn 181    wgreerqsvf pfesgkpfki qvlvepdhfk vavndahllq ynhrvkklne isklgisgdi 241    dltsasytmi SEQ ID NO: 7 Human Gal-3 cDNA Sequence (transcript variant 2)
  1    atggcagaca attttcgct ccatgatgcg ttatctgggt ctggaaaccc aaaccctcaa 61    ggatggcctg gcgcatgggg gaaccagcct gctggggcag gggctaccc aggggcttcc
```

TABLE 1-continued

```
121    tatcctgggg cctacccegg gcaggcacce ccagggget atcctggaca ggcacctcca
181    ggcgectacc ctggagcacc tggagcttat cccgtagcac ctgcacctgg agtctaccca
241    gggccaccca gcggccctgg ggcctaccca tcttctggac agccaagtgc caccggagcc
301    taccctgcca ctggccccta tggcgcccct gctgggccac tgactgtgcc ttataacctg
361    cctttgcctg ggggagtggt gcctcgcatg ctgataacaa ttctgggcac ggtgaagccc
421    aatgcaaaca gaattgcttt agatttccaa agagggaatg atgttgcctt ccactttaac
481    ccacgcttca atgagaacaa caggagagtc attgtttgca cttacatgtg taaaggtttc
541    atgttcactg tgagtgaaaa ttttacatt catcaatatc cctcttgtaa gtcatctact
601    taa
```

SEQ ID NO: 8 Human Gal-3 Amino Acid Sequence (isoform 2)
```
  1    madnfslhda lsgsgnpnpq gwpgawgnqp agaggypgas ypgaypgqap pgaypgqapp
 61    gaypgapgay pgapapgvyp gppsgpgayp ssgqpsatga ypatgpygap agplivpynl
121    plpggvvprm litilgtvkp nanrialdfq rgndvafhfn prfnennrrv ivctymckgf
181    mftvsenfyi hqypscksst
```

SEQ ID NO: 9 Mouse Gal-3 cDNA Sequence (transcript variant 1)
```
  1    atggcagaca gcttttcgct taacgatgcc tagctggct ctggaaaccc aaaccctcaa
 61    ggatatccgg gtgcatgggg gaaccagcct ggggcagggg gctacccagg gctgcttat
121    cctggggcct acccaggaca agctcctcca ggggcctacc caggacaggc tcctccaggg
181    gcctacccag gacaggctcc tctagtgcc taccccggcc caactgcccc tggagcttat
211    cctggcccaa ctgcccctgg agcttatcct ggctcaactg ccctggagc cttcccaggg
301    caacctgggg cacctggggc ctaccccagt gctcctggag gctatcctgc tgctggccct
361    tatggtgtcc ccgctggacc actgacggtg ccctatgacc tgcccttgcc tggaggagtc
421    atgccccgca tgctgatcac aatcatgggc acagtgaaac ccaacgcaaa caggattgtt
481    ctagattca ggagagggaa tgatgttgcc ttccacttta accccgctt caatgagaac
541    aacaggagag tcattgtgtg taacacgaag caggacaata actggggaaa ggaagaaaga
601    cagtcagcct ccccctttga gagtggcaaa ccattcaaaa tacaagtcct ggttgaagct
661    gaccacttca aggttgcggt caacgatgct cacctactgc agtacaacca tcggatgaag
721    aacctccggg aaatcagcca actggggatc agtggtgaca taaccctcac cagcgctaac
781    cacgccatga tctaa
```

SEQ ID NO: 10 Mouse Gal-3 Amino Acid Sequence (isoform 1)
```
  1    madsfslnda lagsgnpnpq gypgawgnqp gaggypgaay pgaypgqapp gaypgqappg
 61    aypgqappsa ypgptapgay pgptapgayp gstapgafpg qpgapgayps apggypaagp
121    ygvpagpltv pydlplpggv mprmlitimg tvkpnanriv ldfrrgndva fhfnprfnen
181    nrrvivcntk qdnnwgkeer qsafpfesgk pfkiqvlvea dhfkvavnda hllqynhrmk
241    nlreisqlgi sgditltsan hami
```

SEQ ID NO: 11 Mouse Gal-3 cDNA Sequence (transcript variant 2)
```
  1    atggcagaca gcttttcgct taacgatgcc tagctggct ctggaaaccc aaaccctcaa
 61    ggatatccgg gtgcatgggg gaaccagcct ggggcagggg gctacccagg gccgcttac
121    cctggggcct acccaggaca agctcctcca ggggcctacc caggacaggc tcctccaggg
161    gcctacccag gacaggctcc tctagtgcc taccccggcc caactgcccc tggagcttat
241    cctggcccaa ctgcccctgg agcttatcct ggctcaactg ccctggagc cttcccaggg
301    caacctgggg cacctggggc ctaccccagt gctcctggag gctatcctgc tgctggccct
```

TABLE 1-continued

```
361    tatggtgtcc ccgctggacc actgacggtg ccctatgacc tgccctgcc tggaggagtc
421    atgccccgca tgctgatcac aatcatgggc acagtgaaac ccaacgcaaa caggattgtt
481    ctagatttca ggagagggaa tgatgttgcc ttccacttta accccgctt caatgagaac
541    aacaggagag ccattgtgcg taacacgaag caggacaata actggggaaa ggaagaaaga
601    cagtcagcct tccccttga gagtggcaaa ccattcaaaa tacaagtcct ggttgaagct
661    gaccacttca aggttgcggt caacgatgct cacctactgc agtacaacca tcggatgaag
721    aacctccggg aaatcagcca actggggatc agcggtgaca taaccctcac cagcgctaac
781    cacgccatga tctaa
```

SEQ ID NO: 12 Mouse Gal-3 Amino Acid Sequence (isoform 2)
```
  1    madsfslnda lagsgnpnpq gypgawgnqp gaggypgaay pgaypgqapp gaypgqappg
 61    aypgqappsa ypgptapgay pgptapgayp gstapgafpg qpgapgayps apggypaagp
121    ygvpagplcv pydlplpggv mprmlitimg tvkpnanriv ldfrrgndva fhfnprfnen
181    nrrvivcntk qdnnwgkeer qsafpfesgk pfkiqvlvea dhfkvavnda hllqynhrmk
241    nlreisqlgi sgditltsan hami
```

SEQ ID NO: 13 Human Gal-9A cDNA Sequence (transcript variant 1)
```
  1    atggccttca gcggttccca ggctccctac ctgagtccag ctgtcccctt ttctgggact
 61    attcaaggag gtctccagga cggacttcag atcactgtca atgggaccgt tctcagctcc
121    agtggaacca ggtttgctgt gaacttccag actggcttca gtggaaatga cattgccttc
181    cacttcaacc ctcggtttga agatggaggg tacgtggtgt gcaacacgag gcagaacgga
241    agctggggc cgaggagag aagacacac atgcctctcc agaagggat gcctttgac
301    ctctgcttcc tggtgcagag ctcagatttc aaggtgatgg tgaacgggat cctcttcgtg
361    cagtacttcc accgcgtgcc cttccaccgt gtggacacca tctccgtcaa tggctctgtg
421    cagctgtcct acatcagctt ccagaacccc cgcacagtcc ctgttcagcc tgccttctcc
481    acggtgccgt tctcccagcc tgtctgtttc ccacccaggc caggggcg cagacaaaaa
541    cctccccgcg tgtggcctgc caacccggct cccattccc agacagtcat ccacacagtg
601    cagagcgccc ctggacagat gttctctact ccgccatcc cacctatgat gtacccccac
661    cccgcctatc cgatgccttt catcaccacc attctgggag gctgtaccc atccaagtcc
721    atcctcctgt caggcactgt cctgcccagt gctcagaggt tccacatcaa cctgtgctct
781    gggaaccaca tcgccttcca cctgaacccc gttttgatg agaatgctgt ggtccgcaac
841    acccagatcg acaactcctg ggggtctgag agcgaagtc tgccccgaaa aatgcccttc
901    gtccgtggcc agagcttctc agtgtggatc ttgtgtgaag ctcactgcct caaggtggcc
961    gtggatggtc agcacctgtt tgaatactac catcgcctga ggaacctgcc caccatcaac
1021   agactggaag tgggggggcga catccagctg acccatgtgc agacatag
```

SEQ ID NO: 14 Human Gal-9A Amino Acid Sequence (isoform 1)
```
  1    mafsgsqapy lspavpfsgt iqgglqdglq itvngtvlss sgtrfavnfq tgfsgndiaf
 61    hfnprfedgg yvvcntrqng swgpeerkth mpfqkgmpfd lcflvqssdf kvmvngilfv
121    qyfhrvpfhr vdtisvngsv qlsyisfqnp rtvpvqpafs tvpfsqpvcf pprprgrrqk
181    ppgvwpanpa pitqtvihtv qsapgqmfst paippmmyph paypmpfitt ilgglypsks
241    illsgtvlps aqrfhinlcs gnhiafhlnp rfdenavvra tqidnswgse erslprkmpf
301    vrgqsfsvwi lceahclkva vdgqhlfeyy hrlrnlptin rlevggdiql thvqt
```

TABLE 1-continued

```
SEQ ID NO: 15 Human Gal-9A cDNA Sequence (transcript variant 2)
  1   atggccttca gcggttccca ggctccctac ctgagtccag ctgtcccctt ttctgggact
 61   attcaaggag gtctccagga cggacttcag atcactgtca atgggaccgt tctcagctcc
121   agtggaacca ggtttgctgt gaactttcag actggcttca gtggaaatga cattgccttc
181   cacttcaacc ctcggtttga agatggaggg tacgtggtgt gcaacacgag gcagaacgga
241   agctggggc ccgaggagag gaagacacac atgcctttcc agaaggggat gcccttgac
301   ctctgcttcc tggtgcagag ctcagatttc aaggtgatgg tgaacgggat cctcttcgtg
361   cagtacttcc accgcgtgcc cttccaccgt gtggacacca tctccgtcaa tggctctgtg
421   cagctgtcct acatcagctt ccagcccccc ggcgtgtggc ctgccaaccc ggctcccatt
481   acccagacag tcatccacac agtgcagagc gcccctggac agatgttctc tactcccgcc
541   atcccaccta tgatgtaccc ccaccccgcc tatccgatgc ctttcatcac caccattctg
601   ggagggctgc acccatccaa gtccatcctc ctgtcaggca ctgtcctgcc cagtgctcag
661   aggttccaca tcaacctgtg ctctgggaac cacatcgcct tccacctgaa ccccgtttt
721   gatgagaatg ctgtggtccg caacacccag atcgacaact cctgggggtc tgaggagcga
781   agtccgcccc gaaaaatgcc cttcgcccgt ggccagagct ctcagtgtg gatcttgtgt
841   gaagctcgct gcctcaaggc ggccgtggat ggtcagcacc tgtttgaata ctaccatcgc
901   ctgaggaacc tgcccaccat caacagactg gaagtggggg gcgacatcca gctgacccat
961   gtccagacat ac
SEQ ID NO: 16 Human Gal-9A Amino Acid Sequence (isoform 2)
  1   mafsgsqapy lspavpfsgt iqgglqdglq itvngtvlss sgtrfavnfq tgfsgndiaf
 61   hfnprfedgg yvvcntrqng swgpeerkth mpfqkgmpfd lcflvqssdf kvmvngilfv
121   qyfhrvpfhr vdtisvngsv qlsyisfqpp gvwpanpapi tqtvihtvqs apgqmfstpa
181   ippmmyphpa ypmpfittil gglypsksil lsgtvlpsaq rfhinlcsgn hiafhlnprf
241   denavvrntq idnswgseer slprkmpfvr gqsfsvwilc eahclkvavd gqhlfeyyhr
301   lrnlptinrl evggdiqlth vqt
SEQ ID NO: 17 Human Gal-9B cDNA Sequence
  1   atggccttca gcggttccca ggctccctat ctgagcccag ccgtcccctt ttctgggact
 61   atccaagggg gtctccagga cggatttcag atcactgtca atggggccgt tctcagctcc
121   agtggaacca ggtttgctgt ggactttcag acgggcttca gtggaaacga cattgccttc
181   cacttcaacc ctcggtctga agacggaggg tatgtggtgt gcaacacgag gcagaaagga
241   agatggggc ccgaggagag gaagatgcac atgcccttcc agaaggggat gcccttgac
301   ctctgcttcc tggtgcagag ctcagatttc aaggtgatgg tgaacgggag cctcttcgtg
361   cagcacttcc accgcgtgcc cttccaccgt gtggacacca tctccgtcaa tggctctgtg
421   cagctgtcct acatcagctt ccagaatccc cgcacagtcc cgttcagcc tgcttctcc
481   acggtgccgC tctcccagcc tgtctgtttc ccacccaggc ccaggggcg cagacaaaaa
541   cctcccacgc gtgcggcctgc caacccagct cccattaccc agacagtcat ccacacggtg
601   cagagcgcct ctggacagat gttctctact cccgccatcc cacctatgat gtaccccccac
661   cctgcctatc cgatgccttt catcaccacc atccccggag gctgtaccc atccaagr.cc
721   atcatcctgt caggcactgt cctgcccagt gctcagaggt tccacatcaa cctgtgctct
781   gggagccaca tcgccttcca catgaacccc gttttgatg agaatgctgt ggtccgtaac
841   acccagatca acaactcttg ggggtctgag gagcgaagtc tgccccgaaa aatgcccttc
```

TABLE 1-continued

```
 901   gtccgaggcc agagcttctc ggtgtggatc ttgtgtgaag ctcactgcct caaggtggcc
 961   gtggatggtc agcacgtgtt tgaatactac catcgcctga ggaacctgcc caccatcaac
1021   aaactggaag tgggtggcga catccagctg acccacgtgc agacatag
```

SEQ ID NO: 18 Human Gal-9B Amino Acid Sequence
```
   1   mafsgsqapy lspavpfsgt iqgglqdgfq itvngavlss sgtrfavdfq tgfsgndiaf
  61   hfnprfedgg yvvcntrqkg rwgpeerkmh mpfqkgmpfd lcflvqssdf kvmvngslfv
 121   qyfhrvpfhr vdtisvngsv qlsyisfqnp rtvpvqpafs tvpfsqpvcf pprprgrrqk
 181   ppsvcpanpa pitqtvihtv qsasgqmfst paippmmyph paypmpfitt ipgglypsks
 241   iilsgtvlps aqrfhinlcs gshiafhmnp rfdenavvrn tqinnswgse erslprkmpf
 301   vrgqsfsvwi lceahclkva vdgqhvfeyy hrlrnlptin klevggdiql thvqt
```

SEQ ID NO: 19 Human Gal-9C cDNA Sequence
```
   1   atggccttca gcggttgcca ggctccctat ctgagcccag ccgtcccctt ttctgggact
  61   atccaagggg gtctccagga cggatttcag atcactgtca atggggccgt tctcagctgc
 121   agtggaacca ggtttgctgt ggactttcag acgggcttca gtggaaacga cattgccttc
 181   cacttcaacc ctcggtttga agacggaggg tatgtggtgt gcaacacgag gcagaaagga
 241   acatgggggc ccgaggagag gaagatgcac atgcccttcc agaagggggat gccctttgac
 301   ctctgcttcc tggtgcagag ctcagatctc aaggtgatgg tgaacgggag cctcttcgtg
 361   cagtacttcc accgcgtgcc cttccaccgt gtggacacca tctccgtcaa tggctctgtg
 421   cagctgtcct acatcagctt ccagaatccc cgcgcagtcc cgttcagcc tgcttctcc
 481   acggtgccgt tctcccagcc tgtctgtttc ccacccaggc caggggggcg cagacaaaaa
 541   cctcccagcg tgcggcctgc caacccagct cccattaccc agacagtcat ccacacggtg
 601   cagagtgcct ctggacagat gttctctcag actccgcca tcccacctat gatgtacccc
 661   cacccctgcct atccgatgcc tttcatcacc accactccgg gagggctgta cccatccaag
 721   tccatcatcc tgtcaggcac tgtcctgccc agtgctcaga ggttccacat caacctgtgc
 781   tctgggagcc acatcgcctt ccacatgaac ccccgttttg atgagaatgc tgcggtccgt
 841   aacacccaga tcaacaactc ttgggggtct gaggagcgaa gtctgccccg aaaaatgccc
 901   ttcgtccgag gccagagctt ctcggtgtgg atcttgtgtg aagctcactg cctcaaggtg
 961   gccgtggatg gtcagcacgt gtttgaatac taccatcgcc tgaggaacct gcccaccatc
1021   aacaaactgg aagtgggtgg cgacatccag ctgacccacg tgcagacata g
```

SEQ ID NO: 20 Human Gal-9C Amino Acid Sequence
```
   1   mafsgcqapy lspavpfsgt iqgglqdgfq itvngavlsc sgtrfavdfq tgfsgndiaf
  61   hfnprfedgg yvvcntrqkg twgpeerkmh mpfqkgmpfd lcflvqssdf kvmvngslfv
 121   qyfhrvpfhr vdtisvngsv qlsyisfqnp ravpvqpafs tvpfsqpvcf pprprgrrqk
 181   ppsvrpanpa pitqtvihtv qsasgqmfsq tpaippmmyp hpaypmpfit tipgglypsk
 241   siilagtvlp saqrfhinlc sgshiafhmn prfdenavvr ntqinnswgs eerslprkmp
 301   fvrgqsfsvw ilceahclkv avdgqhvfey yhrlrnlpti nklevggdiq lthvqt
```

SEQ ID NO: 21 Mouse Gal-9 cDNA Sequence (transcript variant 1)
```
   1   atggctctct tcagtgccca gtctccatac attaacccga tcatccccct tactggacca
  61   atccaaggag ggctgcagga gggacttcag gtgacccccc aggggactac caagagtttt
 121   gcacaaaggt tgtggtgaa ctttcagaac agcttcaatg aaatgacat tgccttccac
 161   ttcaaccccc ggtttgagga aggagggtat gtggtttgca cacgaagca gaacggacag
 241   tggggtcctg aggagagaaa gatgcagatg cccttccaga aggggatgcc ctttgagctt
```

TABLE 1-continued

```
 301   cgcttcctgg tgcagaggtc agagttcaag gtgatggtga acaagaaatt ctttgtgcag
 361   taccaacacc gcgtacccta ccacctcgtg acaccatcg ctgtctccgg ctgcttgaag
 421   ctgtccttta tcaccttcca gaactctgca gccctgtcc agcatgtctt ctccacagtg
 481   cagttctctc agccagtcca gttcccacgg accctaagg gcgcaaaca gaaaactcag
 541   aactttcgcc ctgcccacca ggcacccatg gctcaaacta ccatccatat ggttcacagc
 601   acccctggac agatgttctc tactcctgga atccctcctg tggtgtaccc caccccagcc
 661   tataccatac ctttctacac ccccattcca aatgggcttt acccgtccaa gtccatcatg
 721   atatcaggca atgtcttgcc agatgctacg aggttccata ccaaccttcg ctgtggaggt
 781   gacattgctt tccacctgaa ccccgtttc aatgagaatg ctgttgtccg aaacactcag
 841   atcaacaact cctgggggca ggaagagcga agtctgcttg gaggatgcc cttcagtcga
 901   ggccagagct ctcggtgcg gatcatatgt gaaggtcact gcttcaaggt agctgtgaat
 961   ggtcaacaca tgtgtgaata ttaccaccgc ctgaagaact gcaggatat caacactcca
1021   gaagtggcgg gtgatatcca gctgacccac gtgcagacat ag
```

SEQ ID NO: 22 Mouse Gal-9 Amino Acid Sequence (isoform 1)
```
  1   malfsaqspy inpiipftgp iqgglqeglq vtlqgttksf aqrfvvnfqn sfngndiafh
 61   fnprfeeggy vvcntkqngq wgpeerkmqm pfqkgmpfel cflvqrsefk vmvnkkffvq
121   yqhrvpyhlv dtiavsgclk lsfitfqnsa apvqhvfstv qfsqpvqfpr tpkgrkqktq
181   nfrpahqapm aqttihmvhs tpgqmfstpg ippvvyptpa ytipfytpip nglypsksim
241   isgnvlpdat rfhinlrcgg diafhlnprf nenavvrntq innswgqeer sllgrmpfsr
301   gqafavwiic eghcfkvavn gqhmceyyhr lknlqdintl evagdiqlth vqt
```

SEQ ID NO: 23 Mouse Gal-9 cDNA Sequence (transcript variant 2)
```
  1   atggctctct tcagtgccca gtctccatac attaacccga tcatcccctt tactggacca
 61   atccaaggag ggctgcagga gggacttcag gtgaccctcc aggggactac caagagtttt
121   gcacaaaggt ttgtggtgaa ctttcagaac agcttcaatg gaaatgacat tgccctccac
181   ttcaacccc ggtttgagga aggagggtat gtggtttgca cacgaagca gaacggacag
241   tggggtcctg aggagagaaa gatgcagatg cccttccaga aggggatgcc ctttgagctt
301   tgcttcctgg tgcagaggtc agagctcaag gtgatggtga acaagaaatt ctttgtgcag
361   taccaacacc gcgtacccta ccacctcgtg acaccatcg ctgtctccgg ctgcttgaag
421   ccgtccttca ccaccttcca gacLcagaac tttcgtactg cccaccaggc acccatggct
481   caaactacca tccatatggt tcacagcacc ctggacaga tgttctctac tcctggaatc
541   cctcctgtgg tgtaccccac cccagcctat accatacctt tctacacccc cattccaaat
601   gggctttacc cgtccaagtc catcatgata tcaggcaatg tcttgccaga tgctacgagg
661   ttccatatca accctcgctg tggaggtgac attgctttcc acctgaaccc ccgtttcaat
721   gagaatgctg ccgtccgaaa cactcagatc aacaactcct ggggcagga agagcgaagt
781   ctgcttggga ggatgccctt cagtcgaggc agagcttct cggtgtggat catatgtgaa
841   ggtcactgct tcaaggtagc tgtgaatggt caacacatgt gtgaatatta ccaccgcctg
901   aagaacttgc aggatatcaa cactctagaa gtggcgggtg atatccagct gacccacgtg
961   cagacatag
```

SEQ ID NO: 24 Mouse Gal-9 Amino Acid Sequence (isoform 2)
```
  1   malfsaqspy inpiipftgp iqgglqeglq vtlqgttksf aqrfvvnfqn sfngndiafh
 61   fnprfeeggy vvcntkqngq wgpeerkmqm pfqkgmpfel cflvqrsefk vmvnkkffvq
121   yqhrvpyhlv dtiavsgclk lsfitfqtqn frpahqapma qttihmvhst pgqmfstpgi
```

TABLE 1-continued

```
181    ppvvyptpay tipfytpipn glypsksimi sgnvlpdatr fhinlrcggd iafhlnprfn
241    enavvrntqi nnswgqeers llgrmpfsrg qsfsvwiice ghcfkvavng qhmceyyhrl
301    knlqdintle vagdiqlthv qt
```

II. Subjects

In one embodiment, the subject for whom predicted likelihood of efficacy of an anti-immune checkpoint and anti-angiogenesis combination therapy is determined, is a mammal (e.g., mouse, rat, primate, non-human mammal, domestic animal, such as a dog, cat, cow, horse, and the like), and is preferably a human.

In another embodiment of the methods of the present invention, the subject has not undergone treatment, such as chemotherapy, radiation therapy, targeted therapy, anti-immune checkpoint, and/or anti-angiogenesis therapy. In still another embodiment, the subject has undergone treatment, such as chemotherapy, radiation therapy, targeted therapy, anti-immune checkpoint, and/or anti-angiogenesis therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to anti-immune checkpoint and anti-angiogenesis combination therapies of many different cancers in subjects such as those described above. In one embodiment, the cancers are solid tumors, such as lung cancer, melanoma, and/or renal cell carcinoma. In another embodiment, the cancer is an epithelial cancer such as, but not limited to, brain cancer (e.g., glioblastomas) bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In still other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment, evaluate a response to an anti-immune checkpoint and anti-angiogenesis combination therapy, and/or evaluate a response to a combination anti-immune checkpoint and anti-angiogenesis combination therapy. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising an anti-immune checkpoint inhibitor and anti-angiogenesis inhibitor (e.g., ipilimumab and bevacizumab) alone or in combination with other anti-cancer agents.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.1, 1.2, 1.3, 1.4, 1.45, 1.5, 1.55, 1.6, 1.65, 1.7, 1.75, 1.8, 1.85, 1.9, 1.95, 2.0, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, 3.0, 3.5, 4.0, 4.5, or 5.0 fold or greater, or any range in between, inclusive. In embodiment, the pre-determined level is the pre-serum or pre-plasma amount or activity of the biomarker and the fold change is determined relative to a post-serum or post-plasma amount or activity of the biomarker. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. For example, sequences that encode anti-Gal-1, anti-Gal-3, and/or anti-Gal-9 immunoglobulins can be detected as nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual, 2nd ed.*, Cold Spring Harbor Laboratory Press, Cold Spring Harbor, N.Y., 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion or a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than $\frac{1}{100}$ or $\frac{1}{1000}$ members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons. N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a biomarker polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Re.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261.1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra: Perry-O'Keefe et al., 1996, *Proc. Natl. Acad. Sci. USA* 93:14670-675).

In another embodiment. PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Rev.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, *Nucleic Acids Res.* 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.ni.nm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al, supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. For example, biomarker polypeptides or variants thereof can be cloned or amplified in order to therapeutically increase anti-Gal-1, anti-Gal-3, and/or anti-Gal-9 activity to enhance anti-cancer effects. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity.

In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see. e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants or a protein of the present invention (Arkin and Yourvan, 1992, *Proc. Natl. Acad. Sci. USA* 89:7811-7815 Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells (using baculovirus expression vectors), yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a 77 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press. San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Re.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYcpSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983. *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989. *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation. DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of anti-immune checkpoint and anti-angiogenesis combination treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radio-isotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in sin to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible rumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols. *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see. e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos. 6,618,6796; 6,379,897; 6,664,377; 6,451,536; 548,257; U.S. 20030157485 and Schena et al. (1995) Science 20, 467-470; Gerhold et al. (1999) Trends In Biochem. Sci. 24, 168-173; and Lennon et al. (2000) Drug Discovery Today 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to an anti-immune checkpoint and anti-angiogenesis combination therapy. Any method known in the art for detecting polypeptides can be used. Such methods include, but are not limited to, immunodiffusion, immunoelectrophoresis, radioinmmunuoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a biomarker antibody is labeled (with a radioisotope such as $^{125}$I or $^{35}$S, or an assayable enzyme, such as horseradish peroxidase or alkaline phosphatase), and is brought together with the unlabelled sample, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable. When determining the presence, amount, and/or activity of anti-galectin antibodies in a biological sample (e.g., blood, serum, plasma, and the like), antigen can be immobilized and the test sample containing such anti-galectin antibodies can be contacted with the immobilized antigen. The description provided below can be adapted according to well known methods for immobilized antigens used to profile antibodies in a test sample (see, for example, US Pats. Publ. 2009/0075305, 2014/0045199, and 2012/0122723 and U.S. Pat. No. 8,278, 057). In some embodiments, a protein chip, bead, or other solid support system is used whereby, for example, galectin target proteins of interest are comprised directly or indirectly on a protein chip array and antibodies that bind the galectin target proteins of interests are contacted with the bound target antigen.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it as not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$M, $10^{-11}$M, $10^{-12}$M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242:423-426 (1988) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

3. Anti-Cancer Therapies

The efficacy of anti-immune checkpoint and anti-angiogenesis combination therapy is predicted according to biomarker amount and/or activity associated with a cancer in a subject according to the methods described herein. In one embodiment, such anti-immune checkpoint and anti-angiogenesis combination therapy (e.g., anti-CTLA4 and anti-VEGF antibodies) can be administered once a subject is indicated as being a likely responder to anti-immune checkpoint and anti-angiogenesis combination therapy. In another embodiment, such anti-immune checkpoint and anti-angiogenesis combination therapy can be avoided once a subject is indicated as not being a likely responder to anti-immune checkpoint and anti-angiogenesis combination therapy and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint and anti-angiogenesis combination therapy.

The term "targeted therapy" refers to administration of agents that selectively interact with a chosen biomolecule to thereby treat cancer. For example, anti-Gal-1, anti-Gal-3, and/or anti-Gal-9 agents, such as therapeutic monoclonal blocking antibodies, which are well-known in the art and described above, can be used to target tumor microenvironments and cells expressing unwanted Gal-1, Gal-3, and Gal-9 respectively. Similarly, bevacizumab (Avastin™) is a humanized monoclonal antibody that targets vascular endothelial growth factor (see, for example, U.S. Pat. Publ. 2013/0121999, WO 20131083499, and Presta et al. (1997) *Cancer Rev.* 57:4593-4599).

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids; vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BS1-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q. et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H. et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It as also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-immune checkpoint and anti-angiogenesis combination therapies may vary according to the particular anti-immune checkpoint agent and/or anti-angiogenesis agent. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the present invention, the gene delivery vehicle comprises a promoter and a demethylase coding sequence.

Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Feigner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777, 127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy, such as anti-immune checkpoint and anti-angiogenesis combination therapies, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint and anti-angiogenesis combination therapeutic regimen is at least 25%, 30%, 35%, 40%, 45%, 50%, 55%, 60%, 65%, 70%, 75%, 80%, 85%, or more.

Additional criteria for evaluating the response to anti-immune checkpoint and anti-angiogenesis combination therapies are related to "survival," which includes all of the following: survival until mortality, also known as overall survival (wherein said mortality may be either irrespective of cause or rumor related); "recurrence-free survival" (wherein the term recurrence shall include both localized and distant recurrence), metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-immune checkpoint and anti-angiogenesis combination therapeutic regimen can be administered to a population of subjects and the outcome can be correlated to biomarker measurements that were determined prior to administration of any anti-immune checkpoint and anti-angiogenesis combination therapy. The outcome measurement may be pathologic response to therapy given in the neoadjuvant setting. Alternatively, outcome measures, such as overall survival and disease-free survival can be monitored over a period of time for subjects following anti-immune checkpoint and anti-angiogenesis combination therapy for whom biomarker measurement values are known. In certain embodiments, the same doses of anti-immune checkpoint and/or anti-angiogenesis combination agents are administered to each subject. In related embodiments, the doses administered are standard doses known in the art for anti-immune checkpoint and/or anti-angiogenesis combination agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-immune checkpoint and anti-angiogenesis combination therapy can be determined using methods such as those described in the Examples section.

5. Further Uses and Methods of the Present Invention

The compositions described herein can be used in a variety of diagnostic, prognostic, and therapeutic applications.

a. Screening Methods

One aspect of the present invention relates to screening assays, including cell based assays. In one embodiment, the assays provide a method for identifying whether a cancer is likely to respond to anti-immune checkpoint and anti-angiogenesis combination therapy and/or whether an agent can inhibit the growth of or kill a cancer cell that is unlikely to respond to anti-immune checkpoint and anti-angiogenesis combination therapy.

In one embodiment, the present invention relates to assays for screening test agents which bind to, or modulate the biological activity of, at least one antibody that specifically binds a biomarker listed in Table 1, or antigen-binding fragment thereof. In one embodiment, a method for identifying such an agent entails determining the ability of the agent to modulate, e.g. enhance, the at least one antibody that specifically binds a biomarker listed in Table 1, or antigen-binding fragment thereof.

In one embodiment, an assay is a cell-based assay, comprising contacting one or more cancer cells comprised within a B cell population with a test agent and determining of the ability of the test agent to increase the amount or activity of at least one antibody that specifically binds a biomarker listed in Table 1, or antigen-binding fragment thereof.

Analyte proteins (or their respective target polypeptides or molecules) can be coupled with a radioisotope or enzymatic label such that binding can be determined by detecting the labeled protein or molecule in a complex. For example, the proteins can be labeled with $^{125}I$, $^{35}S$, $^{14}C$, or $^{3}H$, either directly or indirectly, and the radioisotope detected by direct counting of radioemission or by scintillation counting. Alternatively, the proteins can be enzymatically labeled with, for example, horseradish peroxidase, alkaline phosphatase, or luciferase, and the enzymatic label detected by determination of conversion of an appropriate substrate to product. Determining interactions between reactants can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of at least one antibody that specifically binds a biomarker listed in Table 1, or antigen-binding fragment thereof, in the context of a biological sample (e.g., blood, serum, cells, or tissue) to thereby determine whether an individual afflicted with a cancer is likely to respond to anti-immune checkpoint and anti-angiogenesis combination therapy, whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can determine at least one antibody that specifically binds to one ore more biomarkers listed in Table 1, or antigen-binding fragment thereof (e.g., Gal-1, Gal-3, Gal-9, and combinations thereof).

Another aspect of the present invention pertains to monitoring the influence of agents (e.g., drugs, compounds, and small nucleic acid-based molecules) on the expression or activity of at least one antibody that specifically binds a biomarker listed in Table 1, or antigen-binding fragment thereof. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to anti-immune checkpoint and anti-angiogenesis combination therapy. In some embodiments, the present invention is useful for classifying a sample (e.g., from a subject) as associated with or at risk for responding to or not responding to anti-immune checkpoint and anti-angiogenesis combination therapy using a statistical algorithm and/or empirical data (e.g., the amount or activity of at least one antibody that specifically binds a biomarker listed in Table 1, or antigen-binding fragment thereof).

An exemplary method for detecting the amount or activity of at least one antibody that specifically binds a biomarker listed in Table 1, or antigen-binding fragment thereof, and thus useful for classifying whether a sample is likely or unlikely to respond to anti-immune checkpoint and anti-angiogenesis combination therapy, involves obtaining a biological sample from a test subject and contacting the biological sample with an agent, such as a galectin listed in Table 1, or a nucleic acid-binding agent like an oligonucleotide, capable of detecting the amount or activity of the at least one antibody that specifically binds a biomarker listed in Table 1, or antigen-binding fragment thereof. In some embodiments, at least one galectin is used, wherein two, three, four, five, six, seven, eight, nine, ten, or more such galectins be used in combination (e.g., Gal-1, Gal-3, and Gal-9, as well as other galectins as negative controls) or in serial. Similarly, at least one In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-immune checkpoint and anti-angiogenesis combination therapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms. Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to anti-immune checkpoint therapy), a biological sample from the subject during remission, or a biological sample from the subject during treatment for developing a cancer progressing despite anti-immune checkpoint therapy.

d. Prognostic Assays

The diagnostic methods described herein can furthermore be utilized to identify subjects having or at risk of developing a cancer that is likely or unlikely to be responsive to anti-immune checkpoint and anti-angiogenesis combination therapy. The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The compositions described herein (including anti-Gal-1, anti-Gal-3, and/or anti-Gal-9 antibodies and derivatives and conjugates thereof) can be used in a variety of in vitro and in vivo therapeutic applications using the formulations and/or combinations described herein. In one embodiment, anti-immune checkpoint and anti-angiogenesis combination agents can be used to treat cancers determined to be responsive thereto. Moreover, such antibodies can be used in combination with other anti-cancer agents. For example, antibodies that block the interaction between VEGF, PD-L1, PD-L2, and/or CTLA-4 and their receptors (e.g., PD-L1 binding to PD-1, PD-L2 binding to PD-1, and the like) can be used to treat cancer in subjects identified as likely responding thereto.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar, (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the respiration uncoupling agents, or by separately reacting a purified respiration uncoupling agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge to al. (1977) "Pharmaceutical Salts", J. Pharm. Sci. 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the respiration uncoupling agents, or by separately reacting the purified respiration uncoupling agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a respiration uncoupling agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a respiration uncoupling agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more respiration uncoupling agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a respiration uncoupling agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a respiration uncoupling agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more respiration uncoupling agents in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the respiration uncoupling agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXEMPLIFICATION

This invention is further illustrated by the following examples, which should not be construed as limiting.

Example 1: Materials and Methods for Examples 2-4 a. Collection of Patient Plasma

Blood samples were collected from the patients enrolled in the phase I clinical trial of Ipi-Bev (Hodi et al. (2014) *Cancer Immunol. Res.* 2:632-642). Blood samples were collected in Vacutainer™ tubes containing heparin. They were diluted with equal volume of RPM11640 and subjected to Ficoll density gradient separation of PBMC. The supernatant above the PBMC layer was collected and used as plasma. Aliquots of plasma were stored at ≤−20° C.

b. Screening Protein Microarray with Patient Plasma Samples

Antibodies presented in the post sera of 4 patients (3 Ipi-Bev patients and 1 Ipi alone patient) were screened using ProtoArray® Human Protein Microarray V5 (Life Technologies, Grand Island, N.Y.) as guided by the manufacturer. Briefly, the proteins arrays were blocked in the synthetic blocking solutions (Life Technologies) for 1 hour and then incubated with plasma samples diluted in the blocking solution (1:500) overnight at 4° C. The arrays were washed and detected with Alexa Fluor® 647 goat anti-human IgG (Life Technologies). The arrays were scanned and image data were acquired using a GenePix® scanner (Molecular Devices). Image data were analyzed using the ProtoArray® Prospector data analysis software (Life Technologies).

Potential antibody targets were identified using Z factor cutoff of 0.4 as recommended by the manufacturer.

c. Detection of Galectin Antibodies in Patient Plasma Samples by Western Blot Analysis Measurement The presence of galectin-1, -3 and -9 antibodies in patient serum samples were further confirmed by Western blot analysis (Hodi et al. (2014) *Cancer Immunol. Res.* 2:632-642). Briefly, recombinant human galectin-1, -3 and -9 (R&D Systems, Minneapolis, Minn.) were run in SDS gels and transferred onto PVDF membranes. The membranes was blocked with 5% fatty acid free, nuclease- and protease free BAS (Calbiochem, La Jolla, Calif.) in PBS overnight and then incubated with plasma samples that were diluted by 2,000 fold in PBS with 2% fatty acid free, nuclease- and protease free BAS overnight. Antibodies bound to galectins were detected with HRP conjugated goat anti-human IgG antibody (Life Technologies) and visualized with electrochemiluminescence (ECL). In order to compare antibody levels in pre- and post-sera, membranes with galectins were incubated with pre-sera and post-sera samples from the same patients in parallel.

d. Quantitative Analysis of Gal-1, -3 and -9 Antibody in Patient Plasma Samples Using ELISA Recombinant human Gal-1, -3 and -9 proteins and a His tag with 8 His residues (used as background) were coated in TBS onto 96-well plates overnight respectively. The plates were blocked with a BSA free blocking solution (Thermo Scientific, Tewksbury, Mass.) for 1 hour at room temperature (RT). Plasma samples were diluted (1:1,000 to 1:60,000) in the blocking solution containing 0.1% Tween-20 and incubated with the coated galectins or His tag for 1 hour at 4° C. After wash with PBST (PBS plus 0.05% Tween-20), the wells were incubated with Rabbit F(ab')2 HPR anti-human IgG (Southern Biotech, Birmingham, Ala.) diluted at 1:2,000 in the blocking solution containing 0.1% Tween-20 for 1 hour at RT. After washing thoroughly with PBST, the signal was amplified using the ELAST® ELISA Amplification System as guided by the manufacturer (PerkinElmer, Waltham, Mass.). Briefly, the washed wells were incubated with diluted biotinyl-tyramide for 15 minutes at RT. After thorough washing with PBST, the wells were incubated with streptavidin-HRP diluted in PBST+1% BSA for 30 minutes at RT. The wells were washed thoroughly with PBST and developed with TMB (Dako, Carpinteria, Calif.). The reaction was stopped with 1 N HCl. OD at 450 and 570 nm were recorded using a microplate reader. Galectin antibody titer ($OD_{Gal}$) and background ($OD_{His}$) was calculated by subtracting $OD_{570}$ from $OD_{450}$. Fold change of galectin antibody titers in response to treatment were calculated using the following formula: Fold change=$(OD_{Gal}-OD_{His})_{Post}/(OD_{Gal}-OD_{His})_{Pre}$. An increase was considered as significant when the fold change was ≥1.45.

e. Preparation of Biotinylated his-Avi-SUMO Tagged Galectin-1 and -3 (HAS-Gal-1 and -Gal-3)

The Expresso® Biotin Cloning & Expression System (Lucigen, Middleton, Wis.) for production of biotinylated proteins with His, Avi and SUMO tags was used. Primer design and PCR amplification to incorporate His, Avi and SUMO tags into galectin cDNA were performed according to instructions provided by the manufacturer. The primers used for generation of galectin-1 and -3 fusion proteins by PCR include: Gal-1 sense: 5'-CGCGAACAGATTGGAGGTgcttgtggtctggtcgccagcaac (SEQ ID NO: 25); Gal-1 antisense: 5'-GTGGCGGCCGCTCTATTAGtcaaaggccacacatttgatctt (SEQ ID NO: 26); Gal-3 sense: 5'-CGCGAACAGATTGGAGGTgcagacaattttcgctccatgat (SEQ ID NO: 27); and Gal-3 antisense: 5'-GTGGCGGC-CGCTCTATTAGtatcatggtatatgaagcactggt (SEQ ID NO: 28). The resulting PCR fragments were mixed with the pAviTag N-His Vector (Lucigen) and used to transform BIOTIN XCell™ F' Chemically Competent Cells (Lucigen). The insertion of galectin cDNAs with tags were confirmed by PCR and DNA sequencing. Single colonies were picked up and grown in LB overnight. Cell pellets were suspended in PBS with 500 mM NaCl and subjected to sonication. After extraction with 1% Triton X-100, His-tagged proteins were purified using HisPur Ni-NTA Resin (Thermo Scientific) following the instructions provided by the manufacturer. Proteins were eluted using PBS plus 250 mM Imidazole, dialyzed against PBS and stored in aliquots at −20° C. Protein identity and biotinylation were confirmed by Western analysis and ELISA using commercial Gal-1 and -3 antibodies (R&D Systems) and streptavidin-HRP respectively. HAS-Gal-1 and -3 were used to show that serum anti-Gal-1 and anti-Gal-3 antibodies are functional and capable of inhibiting binding of Gal-1 and Gal-3 to CD45.

f. Affinity Purification of Anti-Gal-1 Antibody from Patient Plasma

Recombinant Gal-1 (6 μg) was coupled to the activated NHS magnet beads (40 μl) as guided by the manufacturer (Thermo Scientific). Plasma samples (400 μl) were diluted with PBS (800 μl) and incubated with the Gal-1 coupled beads with rotation for 2 hours at RT. The beads were pulled down with a magnet and washed with PBS 5 times and the antibodies bound were eluted from the beads with 0.1 M glycine (pH 2.5) and neutralized with 1/10 volume of 1 M Tris-Cl (pH 9.0). The antibody fractions were concentrated using an Amicon Ultra filter (Millipore, Billerica, Mass.) and stored in PBS supplemented with 0.02% BSA at 4° C. Anti-Gal-1 IgG content was determined by ELISA using normal human IgG (Life Technologies) as standards.

g. Absorption of Anti-Gal-3 and -9 Antibodies from Plasma Samples

Recombinant Gal-3, Gal-9, or BSA (as control) was coated onto 96-well plates in the coating buffer by incubation overnight at 4° C. The coated plates were washed with PBS and blocked with 2.5% BSA in PBS overnight. Plasma samples were diluted with 3 volumes of PBS and incubated in the control wells or Gal-3 or -9 coated wells overnight at 4° C. This incubation was repeated two more times in fresh BSA, Gal-3 or Gal-9 coated wells. The plasma samples were collected and used in Gal-3/CD45 interaction or Gal-9 induced T cell apoptosis assays.

h. Binding of Galectin- and Galectin-3 to CD45

CD45 (R&D Systems; 25 ng/well for Gal-1 binding or 50 ng/well for Gal-3 binding) was coated onto 96-well plates at 4° C. overnight. The plates were blocked with 2.5% fatty acid free, nuclease- and protease free BSA in PBS for 1 hour at RT. Biotinylated HAS-Gal-1 (25 ng in 50 μl PBS plus 0.05% Tween-20 and 0.1% BSA) or HAS-Gal-3 (50 ng in 50 μl PBS containing 0.1% BSA) was added to each well coated with CD45 and incubated for 1 hour at RT. The plates were washed with PBS (for Gal-3) or PBST (for Gal-1) and incubated with streptavidin-HRP diluted in PBS (for Gal-3) or PBST (for Gal-1) with 1% BSA for 1 hour at RT. After thorough washing with PBS or PBST, substrate TBM (Sigma, St Louis, Mo.) was added to each well and incubated for appropriate time. The reaction was stopped with 0.1 N HCl. OD450 and OD570 were measured in a microplate reader. In some experiments, HAS-Gal-1 was pre-incubated with 60 ng of normal human IgG or affinity purified patient plasma anti-Gal-1 antibody for 1 hour at RT and HAS-Gal-3 was pre-incubated with patient plasma or plasma that had been depleted of anti-Gal-3 antibody for 1 hour at 4° C. before addition to CD45 coated plates.

i. T Cell Preparation and Expansion

PBMC were isolated from cord blood of normal donors using Ficoll™ density gradient separation. T cells were enriched from PBMC using the Dynabeads® Untouched™ Human T cells kit according to the instructions provided by the manufacturer (Life Technologies). T cells were activated and expanded in RPM11640 containing 10% FBS and PHA (5 µg/ml).

j. T Cell Apoptosis Assay

For functional analysis of anti-Gal-9 antibody in plasma, galectin-9 (0.1 µg) was preincubated with plasma pre-absorbed with PBS or Gal-9 in U bottomed 96-well plate for 2 hours at 4° C. PHA-activated T cells ($2\times10^5$ cells) were added to each well and incubated for 16 hours at 37° C., and 5% $CO_2$. Apoptotic cells were detected by staining with FITC-Annexin V and PI and FACS analysis.

k. Statistical Analysis

GraphPad Prism 6 software was used to determine Log-rank (Mantel-Cox) test of association of antibody increase with patient overall survival. The Student t-test was used for statistical analysis of Gal-1/CD45 and Gal-3/CD45 binding and Gal-9 induced T cell apoptosis. Differences with $P<0.05$ were considered as being significant.

Example 2: Ipilimumab Plus Bevacizumab Treatment Potentiates Humoral Immune Response to Gal-1, Gal-3, and Gal-9

Clinical data indicate synergistic effect of Ipi plus Bev on advanced melanoma (metastatic melanoma) patients (Hodi et al. (2014) *Cancer Immunol. Res.* 2:632-642). To understand the acting mechanism(s) behind this synergy, it was determined whether Ipi-Bev induced humoral immune response in patients using Western blot analysis of whole lysates of cultured melanoma cells, tumor associated endothelial cells (TEC), and mesenchymal stem cells (TMSC) with pre- and post-plasma samples of the patients. A number of proteins in the melanoma cells, TEC, and TMSC were recognized by antibodies in the pre-treatment samples. Importantly, new antibody recognitions or enhanced antibody recognitions were detected with the post-treatment samples. These findings indicate that humoral immune response was indeed triggered as function of Ipi-Bev therapy.

To identify the reactive antibodies, protein microarrays with ~9,000 distinct proteins were screened with the post-treatment plasma samples from 3 Ipi-Bev patients and 1 Ipi alone patient. Thousands of hits were generated based on Z-Factor $\geq 0.4$ as recommended by the manufacturer. Because only functional humoral immune responses are relevant to clinical outcomes, antibodies that recognize membrane receptors, extracellular proteins, and/or secreted proteins known to promote tumor growth, angiogenesis, metastasis, and/or immune suppression and evasion were of interest. Among the hits generated from these screenings, antibodies recognizing galectin-1 and -3 were found in post-sera of 3 and 2 out of 4 patients, respectively.

Gal-1 and Gal-3 are of particularly interest because they are well documented to play a key role in tumor growth and progression, angiogenesis, and immune escape. Therefore, it was determined whether Gal-1 and Gal-3 Ig titers changed as a function of Ipi-Bev treatment using Western blot analysis and ELISA. Gal-9 was not included in the protein microarray, but given the biology of galectin-9 in immune regulation, galectin-9 antibody levels in sera from the patients was also determined. Varying levels of Gal-1, -3 and -9 Ig were detected in the pre-treatment plasma samples and Ipi-Bev induced antibody increases were detected in the post-treatment samples by both Western blot analysis and ELISA (FIGS. 1A-1C). An increase in antibody was considered as significant when the fold change (post-/pre-ratio) $\geq 1.5$. Based on this cut-off, an increase in Gal-1 antibody level was detected in 37.2% (16 out of 43) of the Ipi-Bev patients compared to 15.8% (6 out of 38) of the Ipi patients as function of the treatment (FIG. 1D). Increased Gal-3 antibody levels were seen in 32.6% (14 out of 43) of the Ipi-Bev patients, while in 26.3% (10 out of 38) of the Ipi patients (FIG. 1D). These findings indicate that humoral immune responses to Gal-1 and -3 might occur more frequently in Ipi-Bev patients (synergistic therapeutic effect) than Ipi alone patients. An increase by 30% or more was considered a significant change for Gal-9 antibodies. Based on this cut-off value, 18.4% (7 out of 38) and 23.3% (10 out of 43) of the Ipi alone and Ipi-Bev patients displayed an increase in Gal-9 antibody levels, respectively (FIG. 1D).

Figure 2:
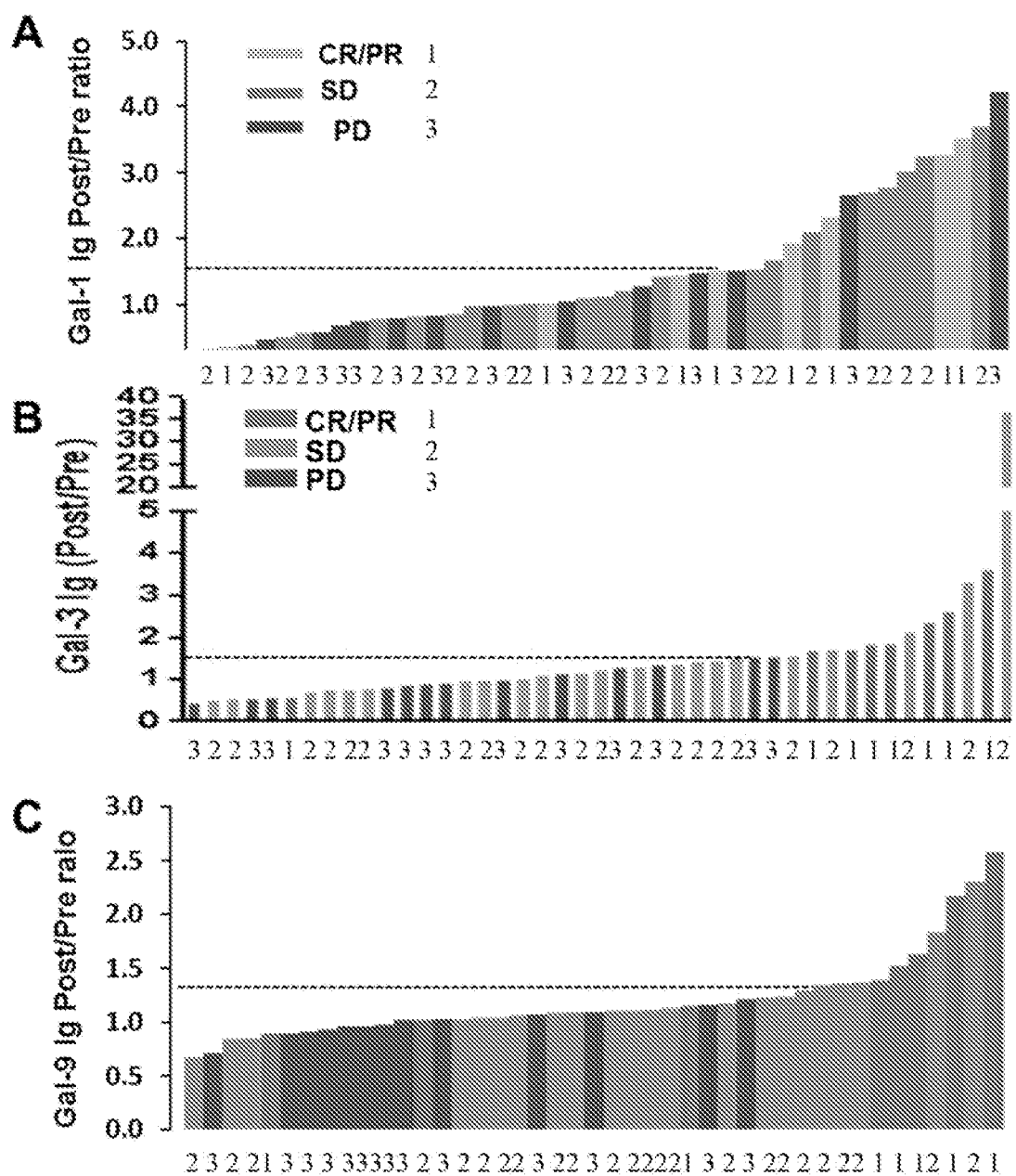
FIG. 2 includes 3 panels, identified as panels A, B, and C, which show that anti-Gal-1, anti-Gal-3, and anti-Gal-9 antibody increased more frequently in patients with CR, PR or SD than those with PD as a function of ipilimumab plus bevacizumab treatment based on a comparison of anti-Gal-1, anti-Gal-3, and anti-Gal-9 Ig fold changes and clinical response, respectively. For panels A-C, patients were ordered based on their antibody fold change (post-/pre-ratio). Clinical responses of each patient are indicated by bar identification. Antibody levels were considered as increased when fold change was ≥1.3 (for Gal-9 Ig) or 1.5 (for Gal-1 and Gal-3 Ig). Dashed lines indicated a fold change of 1.3 (for Gal-9 Ig) or 1.5 (for Gal-1 and Gal-3 Ig).
Figure 3:
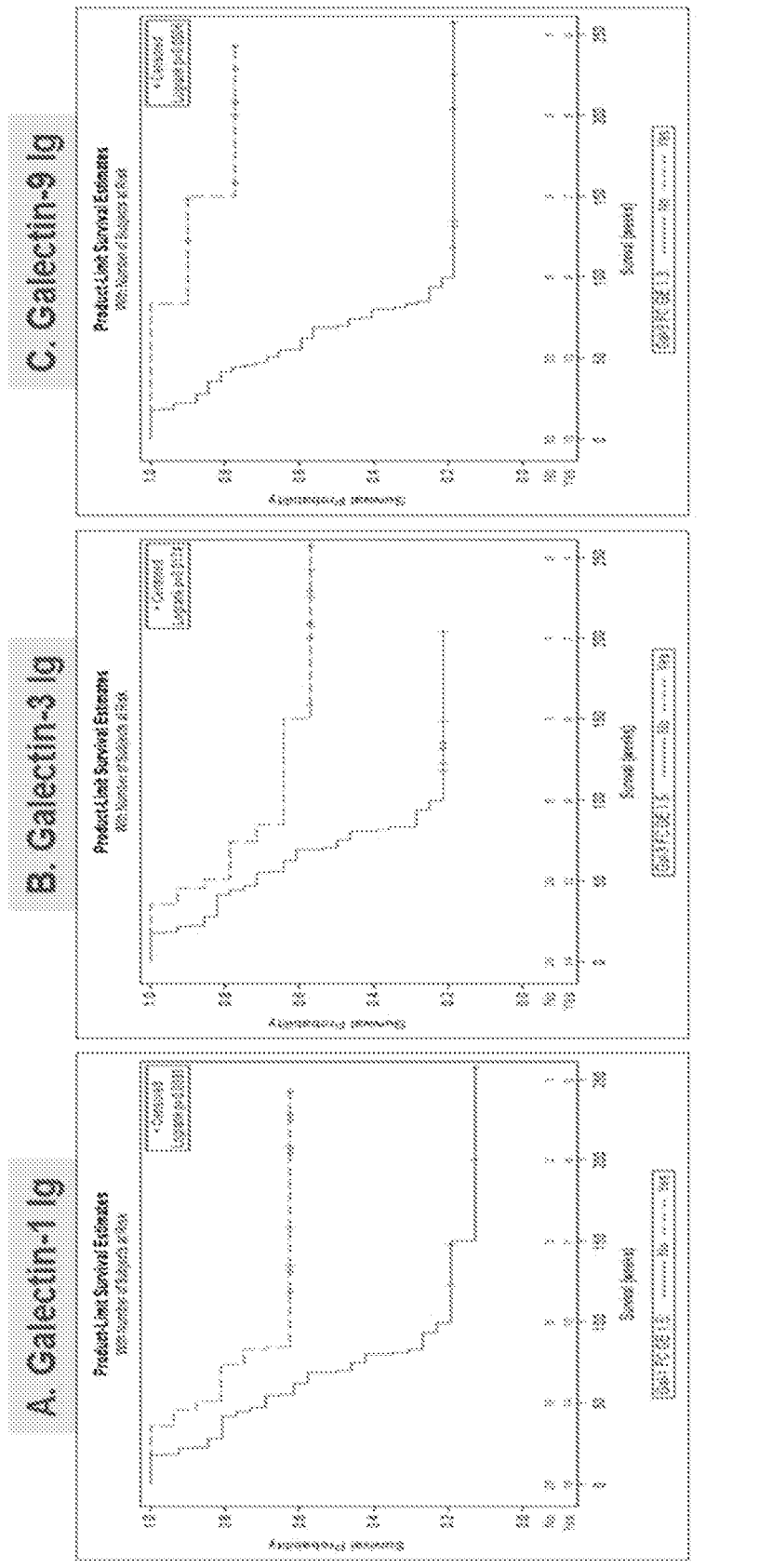
FIG. 3 includes 3 panels, identified as panels A, B, and C, which show that anti-Gal-1, anti-Gal-3, and anti-Gal-9 antibody increase is associated with better survival in metastatic melanoma patients receiving ipilimumab plus bevacizumab. For panels A-C, patients were grouped based on fold changes (post-/pre-ratio) of Gal-1 Ig (panel A; post-/pre-ratio ≥1.5), Gal-3 Ig (panel B; post-/pre-ratio ≥1.5), and Gal-9 Ig (panel C; post-/pre-ratio ≥1.3).
Figure 4:
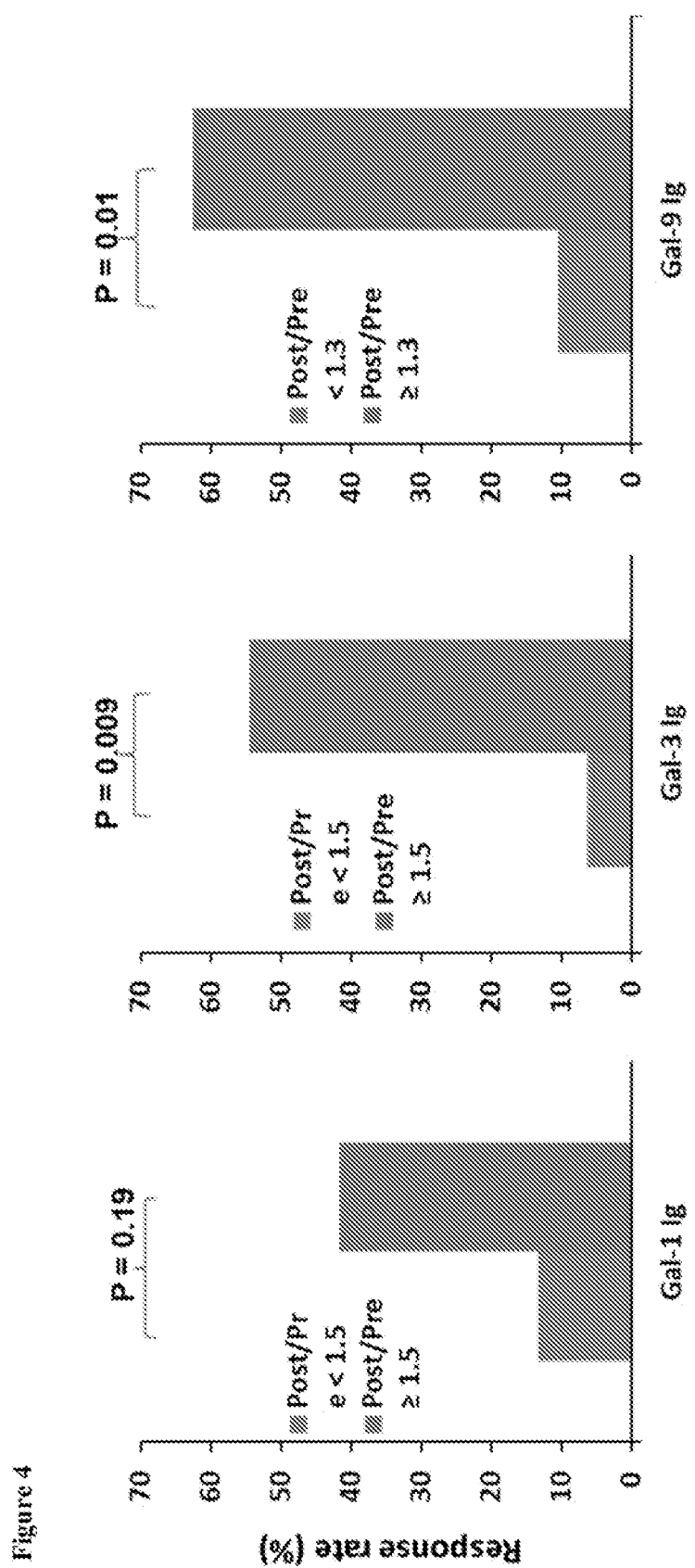
FIG. 4 shows that the increase in Gal-1, Gal-3, and Gal-9 antibodies is associated with higher response rate in metastatic melanoma patients receiving ipilimumab plus bevacizumab.

Example 3: Humoral Immune Response to Gal-1, -3 and -9 is Associated with Clinical Response and Outcomes to Ipi-Bev Therapy It was next examined whether enhanced humoral immune response was associated with clinical outcomes to Ipi-Bev therapy. Among the 16 patients with increased Gal-1 Ig, 5 (31.3%), 8 (50%), and 3 (18.8%) had CR/PR, SD, and PD respectively (FIG. 2A). Gal-1 Ig increase was observed in 62.3% (5 out of 8) of CR and PR patients, 36.4% (8 out of 22) of SD patients, and 23.1% (3 out of 13) of PD patients as function of Ipi-Bev treatment. The mean fold change of Gal-1 antibody in the CR/PR group was significantly greater than that of PD patients (2.51±0.38 vs. 1.33±0.29, p=0.039). The median survival of the patients with the Gal-1 Ig fold change <1.5 was 70 weeks, while that of patients with Gal-1 Ig fold change $\geq 1.5$ was undefined because >50% of the patients were still alive at the time of this analysis (11 months–∞) (FIG. 3A). Among the 14 patients with increased Gal-3 Ig, 7 (50%), 5 (35.7%), and 2 (14.3%) had CR/PR, SD, and PD respectively (FIG. 2B). Gal-3 Ig increase was observed in 87.5% (7 out of 8) of CR and PR patients, 22.7% (5 out of 22) of SD patients, and 15.4% (2 out of 13) of PD patients as function of Ipi-Bev treatment. The median survival of the patients with the Gal-3 Ig fold change <1.5 was 73 weeks, while that of patients with Gal-3 Ig fold change $\geq 1.5$ was undefined (FIG. 3B). Among the 10 patients with increased Gal-9 Ig, 5 (50%), 5 (50%), and 0 (0%) had CR/PR, SD, and PD respectively (FIG. 2C). Gal-9 Ig increase was observed in 71.4% (5 out of 7) of CR and PR patients, 22.7% (5 out of 22) of SD patients, and 0% (0 out of 13) of PD patients as function of Ipi-Bev treatment. The median survival of the patients with the Gal-9 Ig fold change <1.3 was 70 weeks, while that of patients with Gal-9 Ig fold change $\geq 1.3$ was undefined (FIG. 3C). Gal-3 and Gal-9 antibody increase was significantly associated with higher response rate, respectively (FIG. 4). A trend of association of Gal-1 antibody increase with response rate was also noted (FIG. 4). These findings indicate that enhanced humoral immune response to Gal-1, -3 and -9 was associated with better clinical response and overall survival of the patients.

Example 4: Anti-Gal-1, Anti-Gal-3, and Anti-Gal-9 Antibodies are Functional

Figure 5:
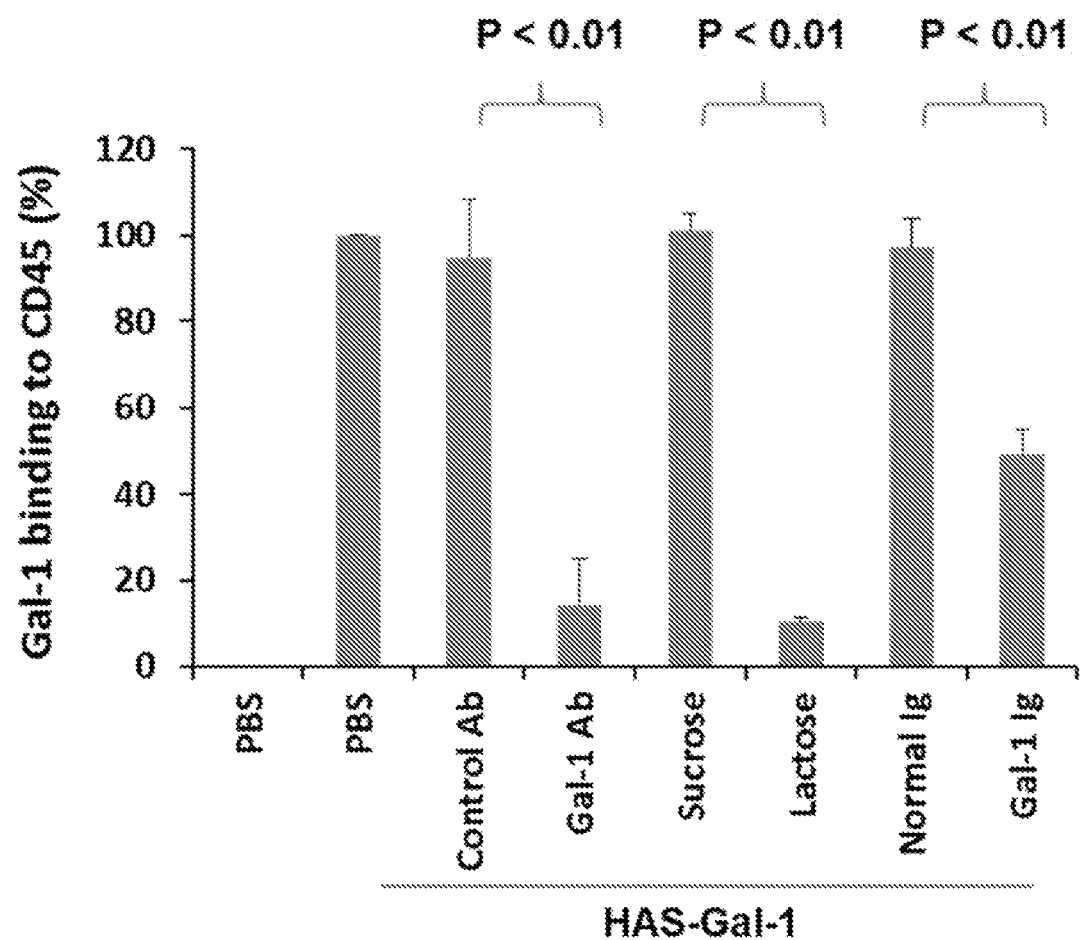
FIG. 5 shows that endogenous anti-Gal-1 antibody abrogates Gal-1 binding to CD45. Anti-galectin-1 antibody was affinity purified from the plasma of a responder. HAS-Gal-1 (25 ng) was incubated with a commercial anti-Gal-1 polyclonal antibody or control antibody (10 μg/ml), purified serum Gal-1 Ig or normal human IgG (1.98 μg/ml) prior to incubation with coated CD45. The binding of HAS-Gal-1 to CD45 was detected with streptavidin-HRP. Sucrose and lactose were added to the reaction at 5 mM. Results are presented as mean±standard deviation (SD) of 3 experiments.
Figure 6:
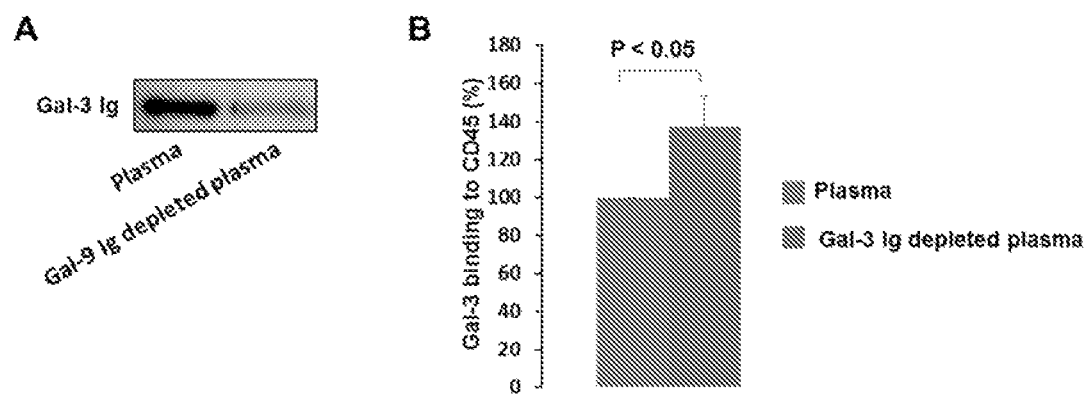
FIG. 6 includes 2 panels, identified as panels A and B, which show that endogenous anti-Gal-3 antibody is functional in neutralizing Gal-3 binding to CD45. Panel A shows that anti-Gal-3 Ig was depleted from the post-plasma of a responder. Panel B shows depletion of anti-Gal-3 Ig from the plasma increased Gal-3 binding to CD45. Binding of Gal-3 to CD45 was detected using recombinant HAS-Gal-3 and CD45. HAS-Gal-3 was incubated with the plasma or plasma depleted of Gal-3 Ig prior to incubation with coated CD45. The mean t SD of 4 independent experiments are shown.
Figure 7:
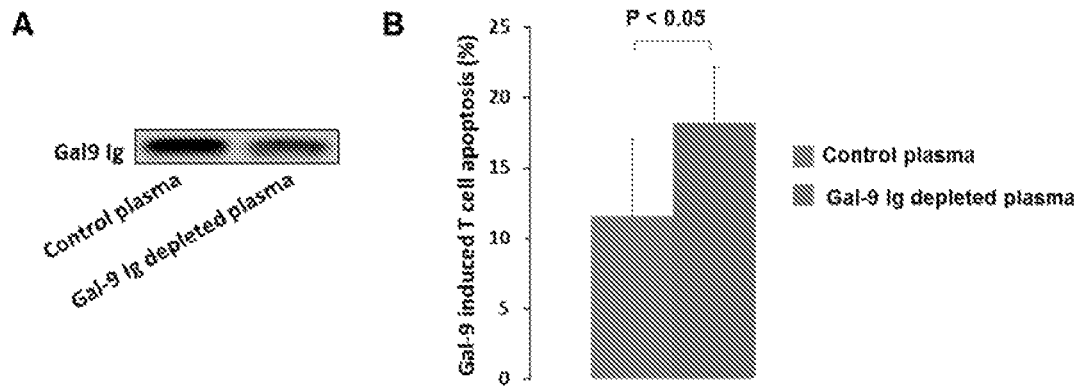
FIG. 7 includes 2 panels, identified as panels A and B, which show that endogenous anti-Gal-9 antibody is functional in neutralizing Gal-9 induced T cell apoptosis. Panel A shows that anti-Gal-9 Ig was depleted from the post plasma of a responder. Panel B shows that depletion of anti-Gal-9 Ig from the plasma increased Gal-9-induced T cell apoptosis. Gal-9 was incubated with the plasma or plasma depleted of anti-Gal-9 Ig prior to addition to T cells. The mean±SD of 5 independent experiments are shown.

It is well known that Gal-1, -3 and -9 promote angiogenesis, tumor growth and immunosuppression. In order to determine if Ipi-Bev induced humeral responses to these galectins are functionally relevant, it was determined whether circulating Gal-1, -3 and -9 antibodies could block biological activities of the galectins. Gal-1, -3 and -9 are well known to induce T cell apoptosis. As binding of Gal-1 or -3 to CD45 induces T cell apoptosis, it was examined whether antibodies recognizing Gal-1 or -3 in the serum of responders could block binding of these galectins to CD45. In order to assess binding of Gal-1 or Gal-3 to CD45, Gal-1 and Gal-3 were expressed in a form having His-SUMO-Biotinylation tags at the N-terminus (HAS-Gal-1 and HAS-Gal-3) in bacterial cells. These fusion proteins were biotinylated and recognized by commercial Gal-1 and -3 antibodies and streptavidin, respectively. Binding of HAS-Gal-1 to CD45 was confirmed to be Gal-1- and glycan-dependent, as this binding was blocked by commercial anti-Gal-1 antibody and β-lactose, but not a control antibody or sucrose (FIG. 5). Similarly, binding of HAS-Gal-3 to CD45 was confirmed to be Gal-3- and glycan-dependent. To test functionality of circulating galectin antibodies, Gal-1 Ig was affinity purified, while Gal-3 and Gal-9 antibody was depleted from the post-sera of responders with increased humoral immune response to the galectin. The purified anti-Gal-1 Ig was capable of inhibiting Gal-1 binding to CD45, while normal human Ig that does not recognize Gal-1 did not (FIG. 5). Depletion of anti-Gal-3 antibody from patient plasma increased the binding of HAS-Gal-3 to CD45 (FIG. 6), indicating inhibitory effects of anti-Gal-3 antibody on binding of Gal-3 to CD45. Gal-9 is known to induce apoptosis of activated T cells. Treatment of PHA activated T cells with Gal-9 for 20 hours induced apoptosis in ~12% of T cells in the presence of post-serum of a responder with humoral immune response to Gal-9, but in ~18% of T cells when anti-Gal-9 antibody was depleted from the serum (FIG. 7). These findings indicate that anti-Gal-9 antibody in the serum could neutralize apoptosis inducing activity of Gal-9. Taken together, these results indicate that anti-Gal-1, Gal-3 and Gal-9 antibodies in patient serum could neutralize the biological activities of these galectins.

Treatment of advanced melanoma with Ipi improved the overall survival (Hodi et al. (2010) *N. Engl. J. Med.* 363: 711-723; Robert et al. (2010) *N. Engl. J. Med.* 364:2517-2526). Recent phase I clinical studies showed synergic effects by addition of Bev to Ipi in metastatic melanoma patients (Hodi et al. (2014) *Cancer Immunol. Res.* 2:632-642). The results described herein describe Ipi-Bev potentiated humoral immune responses to pro-tumor, pro-angiogenesis, and/or immunosuppressive Gal-1, -3 and -9 in substantial portions of advanced melanoma patients. While enhanced humoral immune response to Gal-1 and -3 was also seen in melanoma patients treated with Ipi alone, this occurred in a significantly smaller portion of patients as compared to Ipi-Bev patients. Humoral immune responses to Gal-1, -3 and -9 more frequently occurred in patients with CR, PR or SD than those with PD and associated with better overall survival, thus associated with better clinical outcomes to Ipi-Bev therapy. It is believed that humoral response to these galectins are functionally relevant and are one of the acting mechanisms for the synergy of combining Bev with Ipi. This notion is further supported by in vitro findings that the endogenous galectin antibodies were capable of neutralizing the CD45 binding activity of Gal-1 and -3 and T cell apoptosis inducing activity of Gal-9 that are known to be important for the immune suppressive activity of these galectins. The results described herein demonstrate a new anti-tumor mechanism for cancer immunotherapy by enhancing humoral immune response to Gal-1, -3 and -9 and provide compelling evidence for consideration of addition of functional anti-Gal-1, -3 and/or -9 antibody to immunotherapy or/and anti-angiogenesis therapy of cancer.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A method of treating a cancer in a subject likely to be responsive to a combination therapy against an immune checkpoint and an angiogenesis target, wherein the immune checkpoint is CTLA-4, the angiogenesis target is VEGF, and the combination therapy comprises an anti-CTLA-4 antibody and an anti-VEGF antibody, the method comprising:
   a) obtaining or providing a patient sample from a patient having a cancer, wherein the patient sample is selected from serum, whole blood, and plasma;
   b) measuring the amount of at least one antibody that specifically binds a biomarker selected from the group consisting of Gal-1 polypeptide, Gal-3 polypeptide, and Gal-9 polypeptide, or antigen-binding fragment thereof, in the subject sample;
   c) comparing said amount of the at least one antibody that specifically binds the biomarker, or antigen-binding fragment thereof, in a control sample, wherein the control sample is determined from a cancerous or non-cancerous sample from either the patient or a member of the same species to which the patient belongs,
   wherein a significantly increased amount of the at least one antibody that specifically binds the biomarker, or antigen-binding fragment thereof, in the subject sample relative to the control sample identifies the cancer as being more likely to be responsive to the anti-immune checkpoint and anti-angiogenesis combination therapy; and
   d) administering the combination therapy to the subject determined likely to be responsive to the combination therapy.

2. The method of claim 1, wherein
   a) the subject sample and/or the control sample has not been contacted with either a) any anti-cancer treatment, b) any anti-immune checkpoint agent, or c) any anti-angiogenesis agent;
   b) the subject has not been administered a) any anti-cancer treatment, b) any anti-immune checkpoint agent, or c) any anti-angiogenesis agent;
   c) the at least one antibody or antigen-binding fragment thereof, is assessed by enzyme-linked immunosorbent assay (ELISA), radioimmune assay (RIA), immunochemically, Western blot, or flow cytometry;
   d) the biomarker is immobilized onto a solid support, optionally wherein the solid support is an array, bead, or plate;
   e) the at least one antibody, or antigen-binding fragment thereof, is detected by detecting binding of an anti-IgG antibody against the antibody or antigen-binding fragment thereof; and
   f) the antibody or antigen-binding fragment thereof is a neutralizing antibody or neutralizing antigen-binding fragment thereof.

3. The method of claim 1, further comprising recommending, prescribing, or administering at least one additional anti-cancer therapeutic agent, optionally wherein the at least one additional anti-cancer therapeutic agent is a neutralizing anti-Gal-1 antibody or antigen-binding fragment thereof, a neutralizing anti-Gal-3 antibody or antigen-binding fragment thereof, a neutralizing anti-Gal-9 antibody or antigen-binding fragment thereof, or combinations thereof.

4. The method of claim 1, wherein the cancer is a solid tumor.

5. The method of claim 1, wherein the cancer is melanoma, non-small cell lung cancer (NSCLC), small cell lung cancer (SCLC), bladder cancer, prostate cancer, metastatic hormone-refractory prostate cancer, renal cell cancer, colon cancer, ovarian cancer, or brain glioblastoma multiforme.

6. The method of claim 5, wherein the melanoma is metastatic melanoma.

7. The method of claim 1, wherein the subject is a mammal.

8. The method of claim 7, wherein the mammal is an animal model of cancer.

9. The method of claim 7, wherein the mammal is a human.

10. A method of treating a cancer in a subject less likely to be responsive to anti-immune checkpoint and anti-angiogenesis combination therapy, wherein the immune checkpoint is CTLA-4, the angiogenesis target is VEGF, and the combination therapy comprises an anti-CTLA-4 antibody and an anti-VEGF antibody, the method comprising:
   a) obtaining or providing a patient sample from a patient having a cancer, wherein the patient sample is selected from serum, whole blood, and plasma;
   b) measuring the amount of at least one antibody that specifically binds a biomarker selected from the group consisting of Gal-1 polypeptide, Gal-3 polypeptide, and Gal-9 polypeptide, or antigen-binding fragment thereof, in the subject sample; and
   c) comparing said amount of the at least one antibody that specifically binds the biomarker, or antigen-binding fragment thereof, in a control sample, wherein the control sample is determined from a cancerous or non-cancerous sample from either the patient or a member of the same species to which the patient belongs,
   wherein a significantly decreased amount of the at least one antibody that specifically binds the biomarker, or antigen-binding fragment thereof, in the subject sample relative to the control sample identifies the cancer as being less likely to be responsive to the anti-immune checkpoint and anti-angiogenesis combination therapy; and
   d) administering anti-cancer therapy other than anti-immune checkpoint and anti-angiogenesis combination therapy to the subject determined less likely to be responsive to the anti-immune checkpoint and anti-angiogenesis combination therapy, wherein the anti-cancer therapy is selected from the group consisting of targeted therapy, chemotherapy, radiation therapy, and/or hormonal therapy.

11. The method of claim 10, wherein
   a) the subject sample and/or the control sample has not been contacted with either a) any anti-cancer treatment, b) any anti-immune checkpoint agent, or c) any anti-angiogenesis agent;
   b) the subject has not been administered a) any anti-cancer treatment, b) any anti-immune checkpoint agent, or c) any anti-angiogenesis agent;
   c) the at least one antibody, or antigen-binding fragment thereof, is assessed by enzyme-linked immunosorbent assay (ELISA), radioimmune assay (RIA), immunochemically, Western blot, or flow cytometry;
   d) the biomarker is immobilized onto a solid support, optionally wherein the solid support is an array, bead, or plate;
   e) the at least one antibody, or antigen-binding fragment thereof, is detected by detecting binding of an anti-IgG antibody against the antibody or antigen-binding fragment thereof; and
   f) the antibody or antigen-binding fragment thereof is a neutralizing antibody or neutralizing antigen-binding fragment thereof.

12. The method of claim 10, wherein the cancer is a solid tumor.

13. The method of claim 10, wherein the cancer is melanoma, non-small cell lung cancer (NSCLC), small cell lung cancer (SCLC), bladder cancer, prostate cancer, metastatic hormone-refractory prostate cancer, renal cell cancer, colon cancer, ovarian cancer, or brain glioblastoma multiforme.

14. The method of claim 13, wherein the melanoma is metastatic melanoma.

15. The method of claim 10, wherein the subject is a mammal.

16. The method of claim 15, wherein the mammal is an animal model of cancer.

17. The method of claim 15, wherein the mammal is a human.

* * * * *